US011129889B2

(12) United States Patent
Ruprecht et al.

(10) Patent No.: US 11,129,889 B2
(45) Date of Patent: Sep. 28, 2021

(54) RECOMBINANT HIV EPITOPES AND USES THEREOF

(71) Applicant: The University of Louisiana at Lafayette, Lafayette, LA (US)

(72) Inventors: Ruth M. Ruprecht, Lafayette, LA (US); Hemant K. Vyas, San Antonio, TX (US)

(*) Notice: Subject to any disclaimer, the term of this patent is extended or adjusted under 35 U.S.C. 154(b) by 0 days.

(21) Appl. No.: 16/348,097

(22) PCT Filed: Nov. 7, 2017

(86) PCT No.: PCT/US2017/060342
§ 371 (c)(1),
(2) Date: May 7, 2019

(87) PCT Pub. No.: WO2018/085815
PCT Pub. Date: May 11, 2018

(65) Prior Publication Data

US 2019/0298820 A1 Oct. 3, 2019

Related U.S. Application Data

(60) Provisional application No. 62/418,729, filed on Nov. 7, 2016.

(51) Int. Cl.
| | |
|---|---|
| *A61K 38/00* | (2006.01) |
| *C07K 16/00* | (2006.01) |
| *A61K 39/00* | (2006.01) |
| *C07K 14/005* | (2006.01) |
| *C07K 16/10* | (2006.01) |
| *A61K 39/21* | (2006.01) |
| *C12N 7/00* | (2006.01) |
| *A61P 31/18* | (2006.01) |
| *A61K 39/12* | (2006.01) |
| *A61P 31/14* | (2006.01) |

(52) U.S. Cl.
CPC .............. *A61K 39/21* (2013.01); *A61K 39/12* (2013.01); *A61P 31/14* (2018.01); *A61P 31/18* (2018.01); *C07K 14/005* (2013.01); *C07K 16/1063* (2013.01); *C12N 7/00* (2013.01); *A61K 2039/55566* (2013.01); *C12N 2740/15034* (2013.01); *C12N 2740/16071* (2013.01); *C12N 2740/16122* (2013.01); *C12N 2740/16134* (2013.01); *C12N 2740/16171* (2013.01); *C12N 2740/16334* (2013.01)

(58) Field of Classification Search
CPC .... C07K 2317/21; C07K 16/00; A61K 39/00; A61K 2039/505; A61P 37/02
See application file for complete search history.

(56) References Cited

U.S. PATENT DOCUMENTS

| | | | | | |
|---|---|---|---|---|---|
| 5,556,744 | A | 9/1996 | Weiner et al. | | |
| 2014/0335119 | A1* | 11/2014 | Vieillard | C07K 16/2803 | 424/188.1 |
| 2015/0071954 | A1* | 3/2015 | Joyce | A61K 39/12 | 424/188.1 |

OTHER PUBLICATIONS

International Search Report and Written Opinion for PCT/US17/60342, dated Feb. 15, 2018.
Heap et al. An antibody specific for the C-terminal tail of the gp41 transmembrane protein of human immunodeficiency virus type 1 mediates post-attachment neutralization, probably through inhibition of virus-cell fusion. Journal of General Virology (May 1, 2005), vol. 86, pp. 1499-1507.

Hollier et al. The C-terminal tail of the gp41 transmembrane envelope glycoprotein of HIV-1 Glades A, B, C, and D may exist in two conformations: an analysis of sequence, structure, and function. Virology (Jul. 5, 2005) vol. 337, No. 2, pp. 284-296.

Damodharan et al. Expression and immunological characterization of cardamom mosaic virus coat protein displaying HIV gp41 epitopes. Microbiol Immunol (May 14, 2013) vol. 57, pp. 374-385.

EPO Extended Search Report for Application No. 17867137.6, dated Jun. 30, 2020.

McLain L. et al, "Stimulation of neutralizing antibodies to human immunodeficiency virus type 1 in three strains of mice immunized with a 22 amino acid peptide of gp41 expressed on the surface of a plant virus", Vaccine, Elsevier, Amsterdam, NL, (Jun. 1, 1996), vol. 14, No. 8, doi:10.1016/0264-410X(95)00229-T, ISSN 0264-410X, pp. 799-810.

Buratti E. et al, "The Neutralizing Antibody Response Against a Conserved Region of Human Immunodeficiency Virus Type 1 GP41 (Amino Acid Residues 731-752) is Uniquely Directed Against a Conformational Epitope", Journal of General Virology, Society for General Microbiology, Spencers Wood, GB, (Nov. 1, 1998), vol. 70, No. 11, ISSN 0022-1317, pp. 2709-2716.

Steckbeck J. et al, "Topology of the C-Terminal Tail of HIV-1 gp41: Differential Exposure of the Kennedy Epitope on Cell and Viral Membranes", PLOS ONE, (Dec. 7, 2010), vol. 5, No. 12, doi:10.1371/journal.pone.0015261, p. e15261.

S. Matthew Cleveland et al, "A region of the C-terminal tail of the gp41 envelope glycoprotein of human immunodeficiency virus type 1 contains a neutralizing epitope: evidence for its exposure on the surface of the virion", Journal of General Virology., GB, (Mar. 1, 2003), vol. 84, No. 3, doi:10.1099/vir.0.18630-0, ISSN 0022-1317, pp. 591-602.

(Continued)

*Primary Examiner* — Barry A Chestnut
(74) *Attorney, Agent, or Firm* — Kean Miller LLP; Lauren Rucinski

(57) ABSTRACT

Provided herein are recombinant nucleic acid sequences derived from the C-terminal domain of the HIV-1 gp41 protein, and more specifically compositions and methods for using these epitopes to develop vaccine protection against HIV. Also provided here are monoclonal antibodies that specifically bind to these recombinant nucleic acid sequences derived from the C-terminal domain of the HIV-1 gp41 protein.

2 Claims, 32 Drawing Sheets

Specification includes a Sequence Listing.

(56) References Cited

OTHER PUBLICATIONS

Tyler D. S. et al, "Identification of Sites Within GP41 That Serve as Targets for Antibody-Dependent Cellular Cytotoxicity by Using Human Monoclonal Antibodies", The Journal of Immunology, American Association of Immunologists, US, (Nov. 15, 1990), vol. 145, No. 10, ISSN 0022-1767, pp. 3276-3282.

Cardoso et al, "Structural Basis of Enhanced Binding of Extended and Helically Constrained Peptide Epitopes of the Broadly Neutralizing HIV-1 Antibody 4E10", Journal of Molecular Biology, Academic Press, United Kingdom, (Jan. 9, 2007), vol. 365, No. 5, doi:10.1016/J.JMB.2006.10.088, ISSN 0022-2836, pp. 1533-1544.

J. D. Nelson et al, "An Affinity-Enhanced Neutralizing Antibody against the Membrane-Proximal External Region of Human Immunodeficiency Virus Type 1 gp41 Recognizes an Epitope between Those of 2F5 and 4E10", Journal of Virology., US, (Apr. 15, 2007), vol. 81, No. 8, doi:10.1128/JVI.02588-06, ISSN 0022-538X, pp. 4033-4043.

Binley James A et al, "Comprehensive cross-clade neutralization analysis of a panel of anti-human immunodeficiency virus type 1 monoclonal antibodies", Journal of Virology, The American Society for Microbiology, US, (Dec. 1, 2004), vol. 78, No. 23, doi:10.1128/JVI.78.23.13232-13252.2004, ISSN 0022-538X, pp. 13232-13252.

\* cited by examiner

Mega alignment of Kennedy Loop sequences in HIV-1 gp41 across various clades

| Sequence Name | < Pos = 698 | | | | | | |
|---|---|---|---|---|---|---|---|
| | 700 | 710 | 720 | 730 | 740 | 750 | 760 |
| Consensus | WYIKIFIMIVGGLIGLRIXFAVLSIVNRVRQGYSPLSFQTHLPAPRGPDRPEGIEEGGERDRDRSI | | | | | | SEQ ID NO 31 |
| 8 Sequences | | | | | | | |
| HIV1-sf162.pro | WYIKIFIMIVGGLIGLRIVFAVLSIVNRVRQGYSPLSFQTREPAPRGPDRPEGIEEGGEKDRDRSS | | | | | | SEQ ID NO 32 |
| HIV-1 BAL.pro | WYIKIFIMIIGGLIGLIGLRIVFSVLSIMNRVRQGYSPLSFQTHLPASRGPDRPGGIEEEGGERDRDRSG | | | | | | SEQ ID NO 33 |
| HIV-1 pNL 4.3.pro | WYIKLFIMIVGGLVGLRIVFAVLSIVNRVRQGYSPLSFQTHLPIPRGPDRPEGIEEGGEGRDRSI | | | | | | SEQ ID NO 34 |
| SHIV-1157ipd3N4.pro | WYIKIFIMIVGGLIGLRIIFAVLSIVNRVRQGYSPLSFQTHLPLPRGADRPEGIEEEGGERDRDRSI | | | | | | SEQ ID NO 35 |
| SHIV-1157ipEL-p.pro | WYIKIFIMIVGGLIGLRIIFAVLSIVSRVRQGYSPLSFQTHLPTPRGPDRPEGIEEGGERDRDRSI | | | | | | SEQ ID NO 36 |
| SHIV-2873Nip.pro | WYIKIFIMIVGGLIGLRIIFAVLSIVNRVRQGYSPLSFQTLTPNPRELDRLRGIEEEGGEQDKDRSI | | | | | | SEQ ID NO 37 |
| SHIV-SF162p4.pro | WYIKIFIMIVGGLVGLRIVFTVLSIVNRVRQGYSPLSFQTRFPAPRGLDRPEGIEEEGGERDRDRSR | | | | | | SEQ ID NO 38 |
| HIV1-1084i.pro | WYIKIFIMIVGGLIGLRIIFAVLSMVNRVRQGYSPLSFQTLTPNPRGPDRLGRIEEEGGEQDRDRSI | | | | | | SEQ ID NO 39 |

Kennedy N-terminal    Kennedy C-terminal

Kennedy Loop

FIG. 2

Sequences for Kennedy Loop recombinant protein and primers for synthesis

K-NTcc (Kennedy Loop N-terminal with cysteine) from HIV-1 consensus sequence
ttctcactct-TCC AGA GTT AGG CAG GTT TAC GGA CAG TCA CCT CTG TTT CAG ACC CTT ACC CCA AGC-ggaggttcgg SEQ ID NO:40
E. coli codon-optimized sequence (ordered from commercial company)
ttctcactct-TGT CGT GTT CGT AGA CAG GGT TAC TCT CCG CTG ACC CTG TTC CAG ACC CCG TGT-ggaggttcgg SEQ ID NO:41
 C   R   V   R   Q   G   Y   S   P   L   S   F   Q   T   L   T   P   C  SEQ ID NO:42

K-CTcc (Kennedy Loop C Terminal with cysteine) from HIV-1 consensus sequence (split it into KT-1C and KT-2C for SOE PCR)
TGT CCG AAC CCG CGT GGT CCG GAC CGT GGT CTG GGT CGT ATC GAA GAA GAA GGT GGT GAA CAG GAC CGT GAC CGT TCT ATC CGT TGT SEQ ID NO:43
 C   P   N   P   R   G   P   D   R   L   G   R   I   E   E   E   G   G   E   Q   D   R   D   R   S   I   R   C  SEQ ID NO:44

KT-1C (Kennedy template 1 with cysteine) from HIV-1 consensus sequence
ttctcactct- TGC CCA AAC CCG AGG GGA CTC GAC AGG CTC GGA AGA ATC GAA GAA GAA GGT GGA SEQ ID NO:45
E. coli codon-optimized sequence (ordered from commercial company)
ttctcactct- TGT CCG AAC CCG CGT GGT CCG GAC CGT GGT CTG GGT CGT ATC GAA GAA GAA GGT GGT SEQ ID NO:46
 C   P   N   P   R   G   P   D   R   L   G   R   I   E   E   E   G   G  SEQ ID NO:98

KT-2C (Kennedy template 2 with cysteine) from HIV-1 consensus sequence
5'- CCGAACCTCCGCATCGAATGGATCTGTCTCTCGTCTTGCTCTCCACCTTCTTC -3' SEQ ID NO:47
                                         E   Q   D   R   D   R   S   I   R  SEQ ID NO:48
E. coli codon-optimized reverse primer
5'- ccgaacctccACAACGGATAGAACGGTCACGGTCCTGTTCACCACCTTCTTCTTC -3' SEQ ID NO:48
Rev template for seq- E   E   E   G   G   E   Q   D   R   D   R   S   I   R   C- with rev primer SEQ ID NO:49

K-SAR (epitope for SAR-1 mAb) with cysteine from HIV-1 consensus sequence
ttctcactct- TGC CTC GGA AGA ATC GAA GAA GAA GGT GGA GAG CAA GAC GAC AGA GAC AGA TGC TGC-ggaggttcgg SEQ ID NO:50
E. coli codon-optimized sequence (ordered from commercial company)
ttctcactct- TGT CTG GGT CGT ATC GAA GAA GAA GGT GGT GAA CAG GAC CGT GAC CGT TCT TGT-ggaggttcgg SEQ ID NO:51
 C   L   G   R   I   E   E   E   G   G   E   Q   D   R   D   R   S   C  SEQ ID NO:52

FIG. 4

Scrambled sequences for Kennedy Loop recombinant protein and primers for synthesis Scram-K-NTcc (scrambled-Kennedy Loop N-terminal with cysteine) from HIV-1 consensus sequence
ttctcactct- TGC CAG CCT TCA AAC TCA CCA AGG AAT CAG CTT TAC TTT GGA GTT AGC CTG AGC -ggaggttcgg

*E.coli* codon-optimized sequence (ordered from commercial company)
ttctcactct- TGT CAG CCG TCT AAC ACC CCG CGT AAC CAG CTG TAC TTC GGT GTT TCT CTG TGT -ggaggttcgg
C Q P S N T P R N Q L Y F G V S L C Scram-K-CTcc (scrambled Kennedy C-terminal with cysteine) from HIV-1 consensus sequence (split it into SC-KT-1 and SC-KT-2 for SOE PCR)
TGTGAACCGGAAATCAACGGTGAACTGCGTGGTGACCCGCCGACCGGTGGTCGTGACGAACAGCGTGAACGTTCTGAAGACGTTATCTGT
C E P E I N G E L R G D P P T G G R D E Q R E R S E D V I C Scram-K-SAK (scrambled Kennedy with cysteine) from HIV-1 consensus sequence
ttctcactct- TGC CAG AGC CGC ATC GAG GAC GAG GAC GGC GAG GGC GGC CGC GAG CGC CTG TGC-ggaggttcgg E.coli codon-optimized (sequence (ordered from commercial company)
ttctcactct- TGC CAG TCT CGT ATC GAA GAC GAA GAC GGT GAA GGT GGT CGT GAA CGT CTG TGC-ggaggttcgg
C Q S R I E D E D G E G G R E R L C SCRAMPER-C (MPER covering epitopes for mAbs 2F5 and 4E10) from HIV-1 consensus sequence
ttctcactct- TGC AAC TTC AAA GCT TGG ATG GAC TCT TGG CTG TGG CTG ACC CGT TCT AAC TGC-ggaggttcgg

*E.coli* codon-optimized sequence (ordered from commercial company)
ttctcactct-TGC AAC TTC AAA GCT TGG CTG GAC TCT TGG CTG TGG CTG ACC CGT TCT AAC TGC-ggaggttcgg
C N F K A W I D S W L W L T R S N C

FIG. 9

Yield of anti-Kennedy mAbs from single B cell sorting and amplification of antibody variable genes Monkey: RTr-11
Lymphocytes analyzed: 3,56,651 cells
Memory B cells analyzed: 8,696 cells
K-CTcc antigen+: 17 (90 cells obtained)

Monkey: RTr-11
Lymphocytes analyzed: 1,88,780 cells
Memory B cells analyzed: 3,787 cells
Scrambled-K-CTcc antigen+: 2 cells Out of 90 K-CTcc specific memory B cells → 29 gamma genes (VH) → 10 VH genes cloned in pfUSE vector → 10 pairs VH and VL tried for expression
17 lambda genes (VL) → 10 VL genes cloned in pFUSE vector
12 Kappa genes (VL)

10 Full length Antibody clones:
- 61p1A1
- 61p1A12
- 61p1B2 → expressed → characterized
- 61p1B3
- 61p1C5 → expressed
- 61p1D3
- 61p1E2 → expressed
- 61p1F4 → expressed
- 61p1F8
- 61p1G1

FIG. 14

Monoclonal antibody genes

61p1B2 VH gene (rhesus macaque):
ATGGAGTTTGGGCTGAGCTGGGTTTTCCTTGTTGCTATTTTAAAAGGTGTCCAGTGTGAGGTGCAGCTGGTGCAGTCTGGGGCTGAGGTG
AAGAAGCCTGGGGCCTCAGTGAAGCTCTCCTGCAAGGCTTCCGGTTATACTTTTAGCAGCTACACAGTATAAACTGGGTGAGACAGGCCCCT
GGACAAGGACTTGAGTGGATGGGATGGATTAACCTAGCAATGATTATACAGGCTATGCACAGAAGTTCCAGGGCAGAGTCACCATGACC
AGGGACACGTCCACGAGAACGGTCTACATGGAGCTGAGAAGCCTGAGATCTGAGGACTGCGCCGTGTATTACTGTGCAAGGGGCGGGGGT
ACAGACTACTGGGGCCAGGGAGTCCTGGTCACCGTCTCCTCAGCT 61p1B2 CH gene (human):
AGCACCAAGGGCCCATCGGTCTTCCCCCTGGCACCCTCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTACATCTGCAACGTGAATCACAAGCCCAGCAAC
ACCAAGGTGGACAAGAAAGTTGAGCCCAAATCTTGTGACAAAACTCACACATGCCCACCGTGCCCAGCACCTGAACTCCTGGGGGGACCG
TCAGTCTTCCTCTTCCCCCCAAAACCCAAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACAAAGCCGCGGGAGGAGCAGTACAACAGC
ACGTACCGTGTGGTCAGCGTCCTCACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAGGTGTACACCCTGCCCCCATCCCGGGAGGAGATG
ACCAAGAACCAGGTCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACGCAGAAGAGCCTCTCCCTGTCTCCGGGTAAATGA

FIG. 15

Monoclonal antibody genes

61p1B2 VL gene (rhesus macaque):

ATGGCCTGGGCTCTGCTGCTCCTCACTCTCCTCACTCAGGAGACACAGGGTCCTGGGCCTTCCTATGTGCTGACTCAGTCCCCTCAGTGTCT
GCGGCCCCAGGGCAGAAGGTCACCATCTCCTGCTCTGGAAGCAGCTCCAACATCGGAGATATCATGTGGTTCCAGCAGTCCCA
GGAACAGGCCCCAAACTCATCTATGGTTCGGGCAATCGGCCCTCAGGGGTCCCTGACGATTCTCTAGTCTCCAGTCTGGCACCTCAGGC
ACGCTGACCATCAATAGACTCCGTCCGAGGACGAGGCGGATTATTACTGTCAGCATGGGATAGGAGCCTGAATGCTCTTTTATTCGGA
GGAGGGACCCGGCTCACCGTCCTA

61p1B2 CL gene (human):

GGTCAGCCCAAGGCTGCCCCCTCGGTCACTCTGTTCCCGCCCTCCTCTGAGGAGCTTCAAGCCAACAAGGCCACACTGGTGTGTCTCATA
AGTGACTTCTACCCGGGAGCCGTGACAGTGGCCTGGAAGGCAGATAGCAGCCCCGTCAAGGCGGGAGTGGAGACCACCACCCTCCAAA
CAAAGCAACAACAAGTACGCGGCCAGCAGTTACCTGAGCCTGACGCCTGAGCAGTGGAAGTCCCACAGAAGCTACAGCTGCCAGGTCACG
CATGAAGGGAGCACCGTGGAGAAGACAGTGGCCCCTACAGAATGTTCATAG

FIG. 16

Monoclonal antibody genes

61p1C5 VH gene (rhesus macaque):
ATGGAGTTTGGGCTGAGCTGGGTTTTCCTTGTTGCTATTTTAAAAGGTGTCCAGTGTGAGGTGCAGCTGGTGCAGTCTGGGGCTGAGGTG
AAGAAGCCTGGGGCCTCAGTGAAGGTCTCCTGCAAGGCTTCCGGTTATATTTTACCAGCTACAGTATAAACTGGGTGAGACAGGCCCCT
GGACAAGGACTTGAGTGGATGGGATGGATTAACCCTAGCAATGATTACACGGCTACGCACAGAGGTTCCAGGGCAGAATCACCATGACC
AGGGACACGTCCACGAGTACAGTCTACATGGAGCTGAGAAACCTGAGAGCTGAGGACTGGCCGTGTATTACTGTGCAAGGGCGGGGAT
ACAGACTACTGGGGCCAGGGAGTCCTGGTCACCGTCTCCTCAGCTAGCACCAAG 61p1C5 CH gene (human):
GGCCCATCGGTCTTCCCCCTGGCACCCTCCTCCAAGAGCACCTCTGGGGGCACAGCGGCCCTGGGCTGCCTGGTCAAGGACTACTTCCCC
GAACCGGTGACGGTGTCGTGGAACTCAGGCGCCCTGACCAGCGGCGTGCACACCTTCCCGGCTGTCCTACAGTCCTCAGGACTCTACTCC
CTCAGCAGCGTGGTGACCGTGCCCTCAGCAGCTTGGGCACCCAGACCTACATCTGCAACGTGAATCACAAGCCCAGCAACACCAAGGTG
GACAAGAAAGTTGAGCCCAAATCTTGTGACAAAACTCACACATGCCCACCGTGCCCAGCACCTGAACTCCTGGGGGGACCGTCAGTCTTC
CTCTTCCCCCCAAAACCCAAGGACACCCTCATGATCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAGTGCAAGGTCTCCAACAAAGCCCTCCCAGCCCC
ATCGAGAAAACCATCTCCAAAGCCAAAGGGCAGCCCCGAGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGAGCAATGGGCAGCCGGAGAACAACTAC
AAGACCACGCCTCCCGTGCTGGACTCCGACGGCTCCTTCTTCCTCTACAGCAAGTCACCGTGGACAAGAGCAGGTGGCAGCAGGGGAAC
GTCTTCTCATGCTCCGTGATGCATGAGGCTCTGCACAACCACTACACGCAGAAGAGCCTCTCCCTGTCTCCGGGTAAATGA

FIG. 17

Monoclonal antibody genes

61p1C5 VL gene (rhesus macaque):
ATGGCCTGGGCTCTGCTGCTGCTCCTCACTCTCCTCACTCAGGACACAGGGTCCTGGGCCTCCTATGTGCTGACTCAGCCGCCCTCAGTGTCT
GCGGCCCCAGGGCAGAGAAGGTCACCATCTCCTGCTCTGGGAGCAGCCAACATCGGAGATATCATGTATCGTGGTACCAGCAGTTCCCA
GGAACAGCCCCCAAAACTCATCTATGGTGCCGGCAATGGCCCTCAGGGGTCCCTGACCGATTCTCTGGCTCCCAGTCTGGCACCTCAGGC
ACGCTGACCATCAATAGACTCCGTCCTGAGGACGAGGCGGATTATTACTGCTCAGCATGGGATAGGAGCCTGAATGCTCTTTTATTCGGA
GGAGGGACCCGGCTGACCGTCCTA 61p1C5 CL gene (human):
GGTCAGCCCAAGGCTGCCCCCTCGGTCACTCTGTTCCCGCCCTCCTCTGAGGAGCTTCAAGCCAACAAGGCCACACTGGTGTGTCTCATA
AGTGACTTCTACCCGGGAGCCGTGACAGTGGCCTGGAAGGCAGATAGCAGCCCCGTCAAGGCGGGAGTGGAGACCACCACCCCCTCCAAA
CAAAGCAACAACAAGTACGCGGCCAGCAGCTATCTGAGCCTGACGCCTGAGCCAGTGGAAGTCCCACAGAAGTACAGTCTGCCAGGTCACG
CATGAAGGGAGCACCGTGGAGAAGACAGTGGCCCCTACAGAATGTTCATAG

FIG. 18

Monoclonal antibody genes

61p1E2 VH gene (rhesus macaque):

ATGGAGTTTGGGCTGAGCTGGGTTTTCCTTGTTGCTATTTTAAAAGGTGTCCAGTGTGAGGTGCAGCTGGTGCAGTCCTGGGCTGAGGTG
AAGAAGCCTGGGGCCTCAGTGAAGGTCTCCTGCAGGGCTTCCGGTTACACTTTTACCAGCGACAGTATAAATTGGGTGAGACAGGCCCCT
GGACAAGGACTTGAGTGGATGGAATGGATTAACCTAGCAATGGAATACGGCTACGCCACAGAAGTTCCAGGGCAGAGTCACCATGGCC
AGGGACACGTCCACGAATACAGCCTACATGGAGCTGAGCAGCCTGACATCTGAGGACACGGCCGTATTTTCTGTGCAAGGGCGGGAAT
ACAGACTACTGGGGCCAGGGGGTCCTGGTCACCGTCTCCTCAGCT

61p1E2 CH gene (human):

AGCACCAAGGGCCCATCGGTCTTCCCCCTGGCACCCTCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTACATCTGCAACGTGAATCACAAGCCCAGCAAC
ACCAAGGTGGACAAGAAAGTTGAGCCCAAATCTTGTGACAAAACTCACACATGCCCACCGTGCCCAGCACCTGAACTCCTGGGGGGACCG
TCAGTCTTCCTCTTCCCCCCAAAACCCAAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACAAAGCCGCGGGAGGAGCAGTACAACAGC
ACGTACCGTGTGGTCAGCGTCCTCACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAGGTGTACACCCTGCCCCCATCCCGGGAGGAGATG
ACCAAGAACCAGGTCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACGCAGAAGAGCCTCTCCCTGTCTCCGGGTAAATGA

FIG. 19

Monoclonal antibody genes

61p1E2 VL gene (rhesus macaque):
ATGGCCTGGGCTCTGCTGCTCCTCACTCTCTGCTGCTCCTCACTCAGGACACAGGGTCCTGGGCCTCCTATGTGCTGACTCAGCCACCCTCAGTGTCT
GCGGCCCAGGGCAGAGGATCATCATCCTGTTCTGGAAGTAGTTCCAACATCGGGAGATATTATGTATCCTGGTACCAGCAGTTCCCA
GGAACAGCCCCCAAACTCATCTATGGTTCCAACAATCGACCCTCAGGGGTCCCTGACCGATTTTCTGGCTCCCAGTCTGGCACCTCCGCC
ACGCTGACCATCAATGGACTCCGGCCTGAGGACGAGGCGGATTATCACTGCTCAGCATGGGATAGAAGCCTGAATGCTCTGTTATTCGGA
GGAGGGACCCGGCTCACCGTCCTA 61p1E2 CL gene (human):
GGTCAGCCCAAGGCTGCCCCCTCGGTCACTCTGTTCCCGCCCTCCTCTGAGGAGCTTCAAGCCAACAAGGCCACACTGGTGTGTCTCATA
AGTGACTTCTACCCGGGAGCCGTGACAGTGGCCTGGAAGGCAGATAGCAGCCCCGTCAAGGCGGGAGTGGAGACCACCACCCTCCAAA
CAAAGCAACAACAAGTACGCGGCCAGCAGCTATCTGAGCCTGACGCCTGAGCAGTGGAAGTCCCACAGAAGCTACAGCTGCCAGGTCACG
CATGAAGGGAGCACCGTGGAGAAGACAGTGGCCCCTACAGAATGTTCATAG

FIG. 20

Monoclonal antibody genes

61p1F4 VH gene (rhesus macaque):
ATGGAGTTTGGGCTGAGCTGGGTTTTCCTTGTTGCTATTTTAAAAGGTGTCCAGTGTCAGGTGCAGTGGTGCAGTCCGGAGGAGGCTTG
GTTCAGCCGGGGGGGTCCCTGAGACTCTCCTGTGCAGCCTCTGGATTCACTTTCAGGAATTATGGCATTCACTGGGTCCGCCAGTCTCCA
GGGGAGGGGACTGGAGTGGGTGACATTTATTTGGTATGATGGAAGTCGAAATATTGGCAGACTCTGTGAAGGGCCGATTCACCATCTCC
AGAGACAATTCCAAGAACACATGGTTTATCTTCAAATGAACAACCTGTATTGGGGACACGGCCGTATATTACTGTGCGAGGTCACGAATC
ACACTGATTGGACCGGTAATTACGGTCTGGACTCATGGGGCCAAGGGGTCGTCACCGTCTCCTCAGCT 61p1F4 CH gene (human):
AGCACCAAGGGCCCATCGGTCTTCCCCCTGGCACCCTCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTACATCTGCAACGTGAATCACAAGCCCAGCAAC
ACCAAGGTGGACAAGAAAGTTGAGCCCAAAACCCAAGGACACCCACATCTGTGACAAAACTCACACATGCCCACCGTGCCCAGCACCTG
TCAGTCTTCCTCTTCCCCCCAAAACCCAAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACAAAGCCGCGGGAGGAGCAGTACAACAGC
ACGTACCGTGTGGTCAGCGTCCTCACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAGGTGTACACCCTGCCCCCATCCCGGGAGGAGATG
ACCAAGAACCAGGTCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACGCAGAAGAGCCTCTCCCTGTCTCCGGGTAAATGA

FIG. 21

Monoclonal antibody genes

61p1F4 VL gene (rhesus macaque):
ATGGCCTGGGCTCTGCTGCTCTCCCTCACTCTCAGGACACAGGGTCCTGGGCCCAGTCTGCCCTGACTCAGCCTCACCCTCAGCGTCT
GGGGCCCCCGGGCAGAGTGCCACCATTACCTGTTCTGGAAGCAGCTCAACATGGAAATAATTACGTTTATTGGTACCAACAAGTCTCC
GGAAAGGCCCCCAAACTCCTCATCTATAATGATAATCTGAGACCCTCGGTTTCTGGCTCCAAGTCTGGCACGTCA
GCCTCCCTGGCCATCACTGGGCTCCAGTCCGAGGATGAGGCTGATTATTACTGCTCAACATGGGATCGCGGCTGGACGGTTTGTTATTC
GGTGGAGGGACCCGGCTTCACCGTCCTA 61p1F4 CL gene (human):
GGTCAGCCCAAGGCTGCCCCTCGGTCACTCTGTTCCCGCCCTCCTCTGAGGAGCTTCAAGCCAACAAGGCCACACTGGTGTGTCTCATA
AGTGACTTCTACCCGGGAGCCGTGACAGTGGCCTGGAAGGCAGATAGCAGCCCGTCAAGGCGGGAGTGGAGACCACCACACCCTCCAAA
CAAGCAACAACAAGTACGCGGCCAGCAGTATCTGACGCCTGAGCCTGAGCAGTGGAAGTCCCACAGAAGCTACAGTGCCAGGTCACG
CATGAAGGAGCACCGTGGAGAAGACAGTGGCCCCTACAGAATGTTCATAG

FIG. 22

Monoclonal antibody genes

61p1D3 VH gene (rhesus macaque):
ATGGAGTTTGGGCTGAGCTGGGTTTTCCTTGTTGCTATTTTAAAAGGTGTCCAGTGTGAGGTGCAGTGTGCAGTCTGGCCCAGGACTG
GTGAAGGCTTCGGAGACCCTGTCCTCACCTGCGCTGTCTGTGGTGGCTCCATCAGCAGTAATTATGGCTGGAGCTGGATCCGCAGCCC
CCAGGGAAGGGCTGGAGTGGATTGCATATATCGGTGGTAGTGGTAACAACTACAACCCCTCCTCAAGAGTCGAGTCACTATT
TCAAAAGACACGTCAAGAACCAGTTCTCCCTGAAGCTGACCTCTGTGACCGCCGGACACGGCCATTTATTACTGTGCGAGATATAAA
ACGGAGGGAGCGACACGGTTTGAGTANTGGAGCCAGGGAGTCCTGGTCACCGTCTCCTCAGCT 61p1D3 CH gene (human):
AGCACCAAGGGCCCATCGGTCTTCCCCCTGGCACCCTCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTACATCTGCAACGTGAATCACAAGCCCAGCAAC
ACCAAGGTGGACAAGAAAGTTGAGCCCAAAATCTTGTGACAAAACTCACACATGCCCACCGTGCCCAGCACCTGAACTCCTGGGGGACCG
TCAGTCTTCCTCTTCCCCCCAAAACCCAAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACAAAGCCGCGGGAGGAGCAGTACAACAGC
ACGTACCGTGTGGTCAGCGTCCTCACCGTCCTGCACCAGGACTGGCTGAATGGCAAGGAGTACAAGTGCAAGGTCTCAACAAAGCCCTC
CCAGCCCCCATCGAGAAAACCATCTCCAAAGCCAAAGGGCAGCCCCGAGAACCAGGTGTACACCCTGCCCCATCCCGGGAGGAGATG
ACCAAGAACCAGGTCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACGCAGAAGAGCCTCTCCCTGTCTCCGGGTAAATGA

FIG. 23

Monoclonal antibody genes

61p1D3 VL gene (rhesus macaque):
ATGGCCTGGGCTCTGCTGCTCCTCACTCTCCTCACTCAGGAGACACAGGGTCCTGGGCCTCCTATGTGCTGACTCAGCCACCCTCAGCGTCT
GAGGCGGCCAGGAAGAGTGTCACCACCTCCTGTTCTGGAAGCACCTCCAACATCGGAAGTAATAGTGTATCCTGGTACCAGCAGCTCCCA
GGAACAGCTCCCAAACTCCTCATCTATTATAATGATGATCAACGAGCCTCAGGTGTCTCTGACGATTCTCTGCCTCCAAGACTGGCACGTCA
GCCTCCCTGGCCATCAGTGGGCTCCAGACCGAGGATGAGGCTGATTATTACTGCGCAGCATGGGATGATAGCCTGAGCGGTCCGTTATTC
GGAGGAGGGACCCGGCTGACCGTCCTA 61p1D3 CL gene (human):
GGTCAGCCCAAGGCTGCCCCCTCGGTCACTCTGTTCCCGCCCTCCTCTGAGGAGCTTCAAGCCAACAAGGCCACACTGGTGTGTCTCATA
AGTGACTTCTACCCGGGAGCCGTGACAGTGGCCTGGAAGGCAGATAGCAGCCCGTCAAGGCGGGAGTGGAGACCACCACCCTCCAAA
CAAAGCAACAACAAGTACGCGGCCAGCAGCTATCTGAGCCTGACGCCTGAGCAGTGGAAGTCCCACAGAAGTACAGCTGCCAGGTCACG
CATGAAGGGAGCACCGTGGAGAAGACAGTGGCCCCTACAGAATGTTCATAG

FIG. 24

Peptide analysis for epitope mapping

LIGLRIIFAVLSIVN 9356
RIIFAVLSIVNRVRQ 9357
AVLSIVNRVRQGTSP 9358
IVNRVRQGYSPLSFQ 9359
VRQGYSPLSFQTLTP 9360
YSPLSFQTLTPNPR

```
                         SEQUENCE LISTING

<160> NUMBER OF SEQ ID NOS: 98

<210> SEQ ID NO 1
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 1
saggwscagc tggtrcaatc cgg                                           23

<210> SEQ ID NO 2
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 2
caggtgacct tgaaggagtc tgg                                           23

<210> SEQ ID NO 3
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 3
saggtgcagy tggtgsagtc tgg                                           23

<210> SEQ ID NO 4
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 4
caggtgcarc tgcaggagtc rgg                                           23

<210> SEQ ID NO 5
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 5
gaggtgcagc tggtgcagtc tgg                                           23

<210> SEQ ID NO 6
<211> LENGTH: 23
<212> TYPE: DNA
<213> ORGANISM: Artificial Sequence
<220> FEATURE:
<223> OTHER INFORMATION: primer/sequence of interest
```

-continued

<400> SEQUENCE: 6
caggtacagc tgcagcagtc agg                                      23

<210> SEQ ID NO 7
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 7
caggtgcagc tggtgcaatc tgg                                      23

<210> SEQ ID NO 8
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 8
cagtctgtrc tgacvcagcc dcc                                      23

<210> SEQ ID NO 9
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 9
cagkctgccc ygaytcagyc tcc                                      23

<210> SEQ ID NO 10
<211> LENGTH: 18
<212> TYPE: DNA
<213> ORGANISM: Artificial Sequence
<220> FEATURE:
<223> OTHER INFORMATION: primer/sequence of interest

<400> SEQUENCE: 10
tcctctgggc tgactcag                                            18

<210> SEQ ID NO 11
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 11
tcctmtgagc tgacacagcc dcc                                      23

<210> SEQ ID NO 12
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 12
cagcytgtgc tgactcartc gcc                                      23

<210> SEQ ID NO 13
<211> LENGTH: 23

```
<212> TYPE: DNA
<213> ORGANISM: Artificial Sequence
<220> FEATURE:
<223> OTHER INFORMATION: primer/sequence of interest

<400> SEQUENCE: 13
magsctrtgc tgactcagcc rrc                                         23

<210> SEQ ID NO 14
<211> LENGTH: 21
<212> TYPE: DNA
<213> ORGANISM: Artificial Sequence
<220> FEATURE:
<223> OTHER INFORMATION: primer/sequence of interest

<400> SEQUENCE: 14
aattttatgc tgactcagcc c                                           21

<210> SEQ ID NO 15
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 15
cagactgtgg tgacycagga gyc                                         23

<210> SEQ ID NO 16
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 16
cagcytgtgc tgactcarcc acc                                         23

<210> SEQ ID NO 17
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 17
caggcagggc tgactcagcc acc                                         23

<210> SEQ ID NO 18
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 18
gacatycaga tgwcccagtc tcc                                         23

<210> SEQ ID NO 19
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 19
```
gataytgtga tgacccagac tcc                          23

<210> SEQ ID NO 20
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 20
saaatwgtrw tgackcagtc tcc                          23

<210> SEQ ID NO 21
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 21
gacatygtgm tgacccagtc tcc                          23

<210> SEQ ID NO 22
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 22
gaaacgacac tcacgcagtc tcc                          23

<210> SEQ ID NO 23
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 23
gawrttgtgm tgacwcagtc tcc                          23

<210> SEQ ID NO 24
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 24
gacattgtgc tgacccagtc tcc                          23

<210> SEQ ID NO 25
<211> LENGTH: 20
<212> TYPE: DNA
<213> ORGANISM: Artificial Sequence
<220> FEATURE:
<223> OTHER INFORMATION: primer/sequence of interest

<400> SEQUENCE: 25
ggacagcckg gaaggtgtgc                              20

<210> SEQ ID NO 26
<211> LENGTH: 24
<212> TYPE: DNA
<213> ORGANISM: Artificial Sequence

```
<220> FEATURE:
<223> OTHER INFORMATION: primer/sequence of interest

<400> SEQUENCE: 26
gcctgagttc cacgacacgg tcac                                              24

<210> SEQ ID NO 27
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 27
ccgcgtactt gttgttgctc tgt                                               23

<210> SEQ ID NO 28
<211> LENGTH: 20
<212> TYPE: DNA
<213> ORGANISM: Artificial Sequence
<220> FEATURE:
<223> OTHER INFORMATION: primer/sequence of interest

<400> SEQUENCE: 28
cagaggaggg cgggaasaga                                                   20

<210> SEQ ID NO 29
<211> LENGTH: 20
<212> TYPE: DNA
<213> ORGANISM: Artificial Sequence
<220> FEATURE:
<223> OTHER INFORMATION: primer/sequence of interest

<400> SEQUENCE: 29
gaggcagttc cagatttcaa                                                   20

<210> SEQ ID NO 30
<211> LENGTH: 23
<212> TYPE: DNA
<213> ORGANISM: Artificial Sequence
<220> FEATURE:
<223> OTHER INFORMATION: primer/sequence of interest

<400> SEQUENCE: 30
ggtgcagcca cagctcgttt gat                                               23

<210> SEQ ID NO 31
<211> LENGTH: 67
<212> TYPE: PRT
<213> ORGANISM: Artificial Sequence
<220> FEATURE:
<223> OTHER INFORMATION: primer/sequence of interest
<220> FEATURE:
<221> NAME/KEY: VARIANT
<222> LOCATION: 19..19
<223> OTHER INFORMATION: Xaa can be any naturally occurring amino acid

<400> SEQUENCE: 31

Trp Tyr Ile Lys Ile Phe Ile Met Ile Val Gly Gly Leu Ile Gly Leu
1               5                   10                  15

Arg Ile Xaa Phe Ala Val Leu Ser Ile Val Asn Arg Val Arg Gln Gly
            20                  25                  30

Tyr Ser Pro Leu Ser Phe Gln Thr His Leu Pro Ala Pro Arg Gly Pro
        35                  40                  45

Asp Arg Pro Glu Gly Ile Glu Glu Glu Gly Gly Glu Arg Asp Arg Asp
```

```
                50                  55                  60
Arg Ser Ile
 65
```

<210> SEQ ID NO 32
<211> LENGTH: 67
<212> TYPE: PRT
<213> ORGANISM: Artificial Sequence
<220> FEATURE:
<223> OTHER INFORMATION: primer/sequence of interest

<400> SEQUENCE: 32

```
Trp Tyr Ile Lys Ile Phe Ile Met Ile Val Gly Gly Leu Ile Gly Leu
 1               5                  10                  15

Arg Ile Val Phe Ala Val Leu Ser Ile Val Asn Arg Val Arg Gln Gly
            20                  25                  30

Tyr Ser Pro Leu Ser Phe Gln Thr Arg Phe Pro Ala Pro Arg Gly Pro
        35                  40                  45

Asp Arg Pro Glu Gly Ile Glu Glu Gly Gly Glu Lys Asp Arg Asp
    50                  55                  60

Arg Ser Ser
 65
```

<210> SEQ ID NO 33
<211> LENGTH: 67
<212> TYPE: PRT
<213> ORGANISM: Artificial Sequence
<220> FEATURE:
<223> OTHER INFORMATION: primer/sequence of interest

<400> SEQUENCE: 33

```
Trp Tyr Ile Lys Ile Phe Ile Met Ile Ile Gly Gly Leu Ile Gly Leu
 1               5                  10                  15

Arg Ile Val Phe Ser Val Leu Ser Ile Met Asn Arg Val Arg Gln Gly
            20                  25                  30

Tyr Ser Pro Leu Ser Phe Gln Thr His Leu Pro Ala Ser Arg Gly Pro
        35                  40                  45

Asp Arg Pro Gly Gly Ile Glu Glu Gly Gly Glu Arg Asp Arg Asp
    50                  55                  60

Arg Ser Gly
 65
```

<210> SEQ ID NO 34
<211> LENGTH: 67
<212> TYPE: PRT
<213> ORGANISM: Artificial Sequence
<220> FEATURE:
<223> OTHER INFORMATION: primer/sequence of interest

<400> SEQUENCE: 34

```
Trp Tyr Ile Lys Leu Phe Ile Met Ile Val Gly Gly Leu Val Gly Leu
 1               5                  10                  15

Arg Ile Val Phe Ala Val Leu Ser Ile Val Asn Arg Val Arg Gln Gly
            20                  25                  30

Tyr Ser Pro Leu Ser Phe Gln Thr His Leu Pro Ile Pro Arg Gly Pro
        35                  40                  45

Asp Arg Pro Glu Gly Ile Glu Glu Gly Gly Glu Arg Gly Arg Asp
    50                  55                  60

Arg Ser Ile
 65
```

<210> SEQ ID NO 35
<211> LENGTH: 67
<212> TYPE: PRT
<213> ORGANISM: Artificial Sequence
<220> FEATURE:
<223> OTHER INFORMATION: primer/sequence of interest

<400> SEQUENCE: 35

Trp Tyr Ile Lys Ile Phe Ile Met Ile Val Gly Gly Leu Ile Gly Leu
1               5                   10                  15

Arg Ile Ile Phe Ala Val Leu Ser Ile Val Asn Arg Val Arg Gln Gly
            20                  25                  30

Tyr Ser Pro Leu Ser Phe Gln Thr His Leu Pro Leu Pro Arg Gly Ala
        35                  40                  45

Asp Arg Pro Glu Gly Ile Glu Glu Gly Gly Glu Arg Asp Arg Asp
    50                  55                  60

Arg Ser Ile
65

<210> SEQ ID NO 36
<211> LENGTH: 67
<212> TYPE: PRT
<213> ORGANISM: Artificial Sequence
<220> FEATURE:
<223> OTHER INFORMATION: primer/sequence of interest

<400> SEQUENCE: 36

Trp Tyr Ile Lys Ile Phe Ile Met Ile Val Gly Gly Leu Ile Gly Leu
1               5                   10                  15

Arg Ile Ile Phe Ala Val Leu Ser Ile Val Ser Arg Val Arg Gln Gly
            20                  25                  30

Tyr Ser Pro Leu Ser Phe Gln Thr His Leu Pro Thr Pro Arg Gly Pro
        35                  40                  45

Asp Arg Pro Glu Gly Ile Glu Glu Gly Gly Glu Arg Asp Arg Asp
    50                  55                  60

Arg Ser Ile
65

<210> SEQ ID NO 37
<211> LENGTH: 67
<212> TYPE: PRT
<213> ORGANISM: Artificial Sequence
<220> FEATURE:
<223> OTHER INFORMATION: primer/sequence of interest

<400> SEQUENCE: 37

Trp Tyr Ile Arg Ile Phe Ile Met Ile Val Gly Gly Leu Ile Gly Leu
1               5                   10                  15

Arg Ile Ile Phe Ala Val Leu Ser Ile Val Asn Arg Val Arg Gln Gly
            20                  25                  30

Tyr Ser Pro Leu Ser Phe Gln Thr Leu Thr Pro Asn Pro Arg Glu Leu
        35                  40                  45

Asp Arg Leu Arg Gly Ile Glu Glu Gly Gly Glu Gln Asp Lys Asp
    50                  55                  60

Arg Ser Ile
65

<210> SEQ ID NO 38
<211> LENGTH: 67

```
<212> TYPE: PRT
<213> ORGANISM: Artificial Sequence
<220> FEATURE:
<223> OTHER INFORMATION: primer/sequence of interest

<400> SEQUENCE: 38

Trp Tyr Ile Lys Ile Phe Ile Met Ile Val Gly Gly Leu Val Gly Leu
1               5                   10                  15

Arg Ile Val Phe Thr Val Leu Ser Ile Val Asn Arg Val Arg Gln Gly
            20                  25                  30

Tyr Ser Pro Leu Ser Phe Gln Thr Arg Phe Pro Ala Pro Arg Gly Leu
        35                  40                  45

Asp Arg Pro Glu Gly Ile Glu Glu Glu Gly Glu Arg Asp Arg Asp
    50                  55                  60

Arg Ser Arg
65

<210> SEQ ID NO 39
<211> LENGTH: 67
<212> TYPE: PRT
<213> ORGANISM: Artificial Sequence
<220> FEATURE:
<223> OTHER INFORMATION: primer/sequence of interest

<400> SEQUENCE: 39

Trp Tyr Ile Lys Ile Phe Ile Met Ile Val Gly Gly Leu Ile Gly Leu
1               5                   10                  15

Arg Ile Ile Phe Ala Val Leu Ser Met Val Asn Arg Val Arg Gln Gly
            20                  25                  30

Tyr Ser Pro Leu Ser Phe Gln Thr Leu Thr Pro Asn Pro Arg Gly Pro
        35                  40                  45

Asp Arg Leu Gly Arg Ile Glu Glu Glu Gly Gly Glu Gln Asp Arg Asp
    50                  55                  60

Arg Ser Ile
65

<210> SEQ ID NO 40
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 40
ttctcactct tccagagtta ggcagggata ctcacctctg tcatttcaga cccttacccc      60
aagcggaggt tcgg                                                       74

<210> SEQ ID NO 41
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 41
ttctcactct tgtcgtgttc gtcagggtta ctctccgctg tctttccaga ccctgacccc      60
gtgtggaggt tcgg                                                       74

<210> SEQ ID NO 42
<211> LENGTH: 18
<212> TYPE: PRT
```

```
<213> ORGANISM: Artificial Sequence
<220> FEATURE:
<223> OTHER INFORMATION: primer/sequence of interest

<400> SEQUENCE: 42

Cys Arg Val Arg Gln Gly Tyr Ser Pro Leu Ser Phe Gln Thr Leu Thr
1               5                   10                  15

Pro Cys

<210> SEQ ID NO 43
<211> LENGTH: 84
<212> TYPE: DNA
<213> ORGANISM: Artificial Sequence
<220> FEATURE:
<223> OTHER INFORMATION: primer/sequence of interest

<400> SEQUENCE: 43
tgtccgaacc cgcgtggtcc ggaccgtctg ggtcgtatcg aagaagaagg tggtgaacag    60
gaccgtgacc gttctatccg ttgt                                          84

<210> SEQ ID NO 44
<211> LENGTH: 28
<212> TYPE: PRT
<213> ORGANISM: Artificial Sequence
<220> FEATURE:
<223> OTHER INFORMATION: primer/sequence of interest

<400> SEQUENCE: 44

Cys Pro Asn Pro Arg Gly Pro Asp Arg Leu Gly Arg Ile Glu Glu Glu
1               5                   10                  15

Gly Gly Glu Gln Asp Arg Asp Arg Ser Ile Arg Cys
            20                  25

<210> SEQ ID NO 45
<211> LENGTH: 64
<212> TYPE: DNA
<213> ORGANISM: Artificial Sequence
<220> FEATURE:
<223> OTHER INFORMATION: primer/sequence of interest

<400> SEQUENCE: 45
ttctcactct tgcccaaacc cgagggacc cgacaggctc ggaagaatcg aagaagaagg    60
tgga                                                                64

<210> SEQ ID NO 46
<211> LENGTH: 64
<212> TYPE: DNA
<213> ORGANISM: Artificial Sequence
<220> FEATURE:
<223> OTHER INFORMATION: primer/sequence of interest

<400> SEQUENCE: 46
ttctcactct tgtccgaacc cgcgtggtcc ggaccgtctg ggtcgtatcg aagaagaagg    60
tggt                                                                64

<210> SEQ ID NO 47
<211> LENGTH: 52
<212> TYPE: DNA
<213> ORGANISM: Artificial Sequence
<220> FEATURE:
<223> OTHER INFORMATION: primer/sequence of interest

<400> SEQUENCE: 47
```
ccgaacctcc gcatcgaatg gatctgtctc tgtcttgctc tccaccttct tc    52

<210> SEQ ID NO 48
<211> LENGTH: 55
<212> TYPE: DNA
<213> ORGANISM: Artificial Sequence
<220> FEATURE:
<223> OTHER INFORMATION: primer/sequence of interest

<400> SEQUENCE: 48
ccgaacctcc acaacggata gaacggtcac ggtcctgttc accaccttct tcttc    55

<210> SEQ ID NO 49
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 49

Glu Glu Glu Gly Gly Glu Gln Asp Arg Asp Arg Ser Ile Arg Cys
1               5                   10                  15

<210> SEQ ID NO 50
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 50
ttctcactct tgcctcggaa gaatcgaaga agaaggtgga gagcaagaca gagacagatg    60
ctgcggaggt tcgg    74

<210> SEQ ID NO 51
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 51
ttctcactct tgtctgggtc gtatcgaaga agaaggtggt gaacaggacc gtgaccgttc    60
ttgtggaggt tcgg    74

<210> SEQ ID NO 52
<211> LENGTH: 18
<212> TYPE: PRT
<213> ORGANISM: Artificial Sequence
<220> FEATURE:
<223> OTHER INFORMATION: primer/sequence of interest

<400> SEQUENCE: 52

Cys Leu Gly Arg Ile Glu Glu Glu Gly Gly Glu Gln Asp Arg Asp Arg
1               5                   10                  15

Ser Cys

<210> SEQ ID NO 53
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 53

```
ttctcactct tcccagcctt caaactcacc aaggaatcag ctttactttg gagttagcct    60
gagcggaggt tcgg                                                      74
```

<210> SEQ ID NO 54
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 54

```
ttctcactct tgtcagccgt ctaacacccc gcgtaaccag ctgtacttcg gtgtttctct    60
gtgtggaggt tcgg                                                      74
```

<210> SEQ ID NO 55
<211> LENGTH: 18
<212> TYPE: PRT
<213> ORGANISM: Artificial Sequence
<220> FEATURE:
<223> OTHER INFORMATION: primer/sequence of interest

<400> SEQUENCE: 55

Cys Gln Pro Ser Asn Thr Pro Arg Asn Gln Leu Tyr Phe Gly Val Ser
1               5                   10                  15

Leu Cys

<210> SEQ ID NO 56
<211> LENGTH: 90
<212> TYPE: DNA
<213> ORGANISM: Artificial Sequence
<220> FEATURE:
<223> OTHER INFORMATION: primer/sequence of interest

<400> SEQUENCE: 56

```
tgtgaaccgg aaatcaacgg tgaactgcgt ggtgacccgc cgaccggtgg tcgtgacgaa    60
cagcgtgaac gttctgaaga cgttatctgt                                     90
```

<210> SEQ ID NO 57
<211> LENGTH: 30
<212> TYPE: PRT
<213> ORGANISM: Artificial Sequence
<220> FEATURE:
<223> OTHER INFORMATION: primer/sequence of interest

<400> SEQUENCE: 57

Cys Glu Pro Glu Ile Asn Gly Glu Leu Arg Gly Asp Pro Pro Thr Gly
1               5                   10                  15

Gly Arg Asp Glu Gln Arg Glu Arg Ser Glu Asp Val Ile Cys
            20                  25                  30

<210> SEQ ID NO 58
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 58

```
ttctcactct tgccagagcc gcatcgagga cgaggacggc gagggcggcc gcgagcgcct    60
gtgcggaggt tcgg                                                      74
```

<210> SEQ ID NO 59
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 59
ttctcactct tgccagtctc gtatcgaaga cgaagacggt gaaggtggtc gtgaacgtct    60
gtgcggaggt tcgg    74

<210> SEQ ID NO 60
<211> LENGTH: 18
<212> TYPE: PRT
<213> ORGANISM: Artificial Sequence
<220> FEATURE:
<223> OTHER INFORMATION: primer/sequence of interest

<400> SEQUENCE: 60

Cys Gln Ser Arg Ile Glu Asp Glu Asp Gly Glu Gly Gly Arg Glu Arg
1               5                   10                  15

Leu Cys

<210> SEQ ID NO 61
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 61
ttctcactct tgcaacttca aagcttggct ggactcttgg ctgtggctga cccgttctaa    60
ctgcggaggt tcgg    74

<210> SEQ ID NO 62
<211> LENGTH: 74
<212> TYPE: DNA
<213> ORGANISM: Artificial Sequence
<220> FEATURE:
<223> OTHER INFORMATION: primer/sequence of interest

<400> SEQUENCE: 62
ttctcactct tgcaacttca aagcttggct ggactcttgg ctgtggctga cccgttctaa    60
ctgcggaggt tcgg    74

<210> SEQ ID NO 63
<211> LENGTH: 18
<212> TYPE: PRT
<213> ORGANISM: Artificial Sequence
<220> FEATURE:
<223> OTHER INFORMATION: primer/sequence of interest

<400> SEQUENCE: 63

Cys Asn Phe Lys Ala Trp Ile Asp Ser Trp Leu Trp Leu Thr Arg Ser
1               5                   10                  15

Asn Cys

<210> SEQ ID NO 64
<211> LENGTH: 405
<212> TYPE: DNA
<213> ORGANISM: Artificial Sequence
<220> FEATURE:
<223> OTHER INFORMATION: primer/sequence of interest

```
<400> SEQUENCE: 64
atggagtttg ggctgagctg ggttttcctt gttgctattt taaaaggtgt ccagtgtgag      60
gtgcagctgg tgcagtctgg ggctgaggtg aagaagcctg ggcctcagt gaagctctcc     120 tgcaaggctt ccggttatac ttttagcagc tacagtataa actgggtgag acaggcccct    180
ggacaaggac ttgagtggat gggatggatt aaccctagca atgattatac aggctatgca    240
cagaagttcc agggcagagt caccatgacc agggacacgt ccacgagaac ggtctacatg    300
gagctgagaa ccctgaaatc tgaggactcg gccgtgtatt actgtgcaag gggcggggt    360 acagactact ggggccaggg agtcctggtc accgtctcct cagct                    405

<210> SEQ ID NO 65
<211> LENGTH: 990
<212> TYPE: DNA
<213> ORGANISM: Artificial Sequence
<220> FEATURE:
<223> OTHER INFORMATION: primer/sequence of interest

<400> SEQUENCE: 65
agcaccaagg gcccatcggt cttccccctg gcaccctcct ccaagagcac ctctgggggc      60
acagcggccc tgggctgcct ggtcaaggac tacttccccg aaccggtgac ggtgtcgtgg    120
aactcaggcg ccctgaccag cggcgtgcac accttcccgg ctgtcctaca gtcctcagga    180
ctctactccc tcagcagcgt ggtgaccgtg ccctccagca gcttgggcac ccagacctac    240
atctgcaacg tgaatcacaa gcccagcaac accaaggtgg acaagaaagt tgagcccaaa    300
tcttgtgaca aaactcacac atgcccaccg tgcccagcac ctgaactcct ggggggaccg    360
tcagtcttcc tcttcccccc aaaacccaag gacaccctca tgatctcccg gacccctgag    420
gtcacatgcg tggtggtgga cgtgagccac gaagaccctg aggtcaagtt caactggtac    480
gtggacggcg tggaggtgca taatgccaag acaaagccgc gggaggagca gtacaacagc    540
acgtaccgtg tggtcagcgt cctcaccgtc ctgcaccagg actggctgaa tggcaaggag    600
tacaagtgca aggtctccaa caaagccctc ccagccccca tcgagaaaac catctccaaa    660
gccaaagggc agccccgaga accacaggtg tacaccctgc ccccatcccg ggaggagatg    720
accaagaacc aggtcagcct gacctgcctg gtcaaaggct tctatcccag cgacatcgcc    780
gtggagtggg agagcaatgg gcagccggag aacaactaca agaccacgcc tcccgtgctg    840
gactccgacg gctccttctt cctctacagc aagctcaccg tggacaagag caggtggcag    900
caggggaacg tcttctcatg ctccgtgatg catgaggctc tgcacaacca ctacacgcag    960
aagagcctct ccctgtctcc gggtaaatga                                      990

<210> SEQ ID NO 66
<211> LENGTH: 384
<212> TYPE: DNA
<213> ORGANISM: Artificial Sequence
<220> FEATURE:
<223> OTHER INFORMATION: primer/sequence of interest

<400> SEQUENCE: 66
atggcctggg ctctgctgct cctcactctc ctcactcagg acacagggtc ctgggcctcc      60
tatgtgctga ctcagtctcc ctcagtgtct gcggccccag gcagaaggt caccatctcc     120 tgctctggag gcagctccaa catcgggaga tatcatgtat cgtggttcca gcagttccca    180
ggaacagccc ccaaactcat ctatggttcc ggcaatcggc cctcagggt ccctgaccga    240 ttctctagct cccagtctgg cacctcaggc acgctgacca tcaatagact ccgtcccgag    300
```
gacgaggcgg attattactg ctcagcatgg gataggagcc tgaatgctct tttattcgga      360
ggagggaccc ggctcaccgt ccta      384

<210> SEQ ID NO 67
<211> LENGTH: 321
<212> TYPE: DNA
<213> ORGANISM: Artificial Sequence
<220> FEATURE:
<223> OTHER INFORMATION: primer/sequence of interest

<400> SEQUENCE: 67
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tatctgagcc tgacgcctga gcagtggaag     240
tcccacagaa gctacagctg ccaggtcacg catgaaggga gcaccgtgga agacagtgtg     300
gcccctacag aatgttcata g      321

<210> SEQ ID NO 68
<211> LENGTH: 414
<212> TYPE: DNA
<213> ORGANISM: Artificial Sequence
<220> FEATURE:
<223> OTHER INFORMATION: primer/sequence of interest

<400> SEQUENCE: 68
atggagtttg ggctgagctg ggttttcctt gttgctattt taaaaggtgt ccagtgtgag      60
gtgcagctgg tgcagtctgg ggctgaggtg aagaagcctg gggcctcagt gaagctctcc     120
tgcaaggctt ccggttatat ttttaccagc tacagtataa actgggtgag acaggcccct     180
ggacaaggac ttgagtggat gggatggatt aaccctagca atgattacac aggctacgca     240
cagaggttcc agggcagaat caccatgacc agggacacgt ccacgagtac agtctacatg     300
gagctgagaa acctgagatc tgaggactcg gccgtgtatt actgtgcaag ggcgcgggat     360
acagactact ggggccaggg agtcctggtc accgtctcct cagctagcac caag           414

<210> SEQ ID NO 69
<211> LENGTH: 981
<212> TYPE: DNA
<213> ORGANISM: Artificial Sequence
<220> FEATURE:
<223> OTHER INFORMATION: primer/sequence of interest

<400> SEQUENCE: 69
ggcccatcgg tcttccccct ggcaccctcc tccaagagca cctctggggg cacagcggcc      60
ctgggctgcc tggtcaagga ctacttcccc gaaccggtga cggtgtcgtg gaactcaggc     120
gccctgacca gcggcgtgca caccttcccg gctgtcctac agtcctcagg actctactcc     180
ctcagcagcg tggtgaccgt gccctccagc agcttgggca cccagaccta catctgcaac     240
gtgaatcaca agcccagcaa caccaaggtg gacaagaaag ttgagcccaa atcttgtgac     300
aaaactcaca catgcccacc gtgcccagca cctgaactcc tggggggacc gtcagtcttc     360
ctcttccccc caaaacccaa ggacaccctc atgatctccc ggacccctga ggtcacatgc     420
gtggtggtgg acgtgagcca cgaagaccct gaggtcaagt tcaactggta cgtggacggc     480
gtggaggtgc ataatgccaa gacaaagccg cgggaggagc agtacaacag cacgtaccgt     540

```
gtggtcagcg tcctcaccgt cctgcaccag gactggctga atggcaagga gtacaagtgc      600
aaggtctcca acaaagccct cccagccccc atcgagaaaa ccatctccaa agccaaaggg      660
cagccccgag aaccacaggt gtacaccctg cccccatccc gggaggagat gaccaagaac      720
caggtcagcc tgacctgcct ggtcaaaggc ttctatccca gcgacatcgc cgtggagtgg      780
gagagcaatg ggcagccgga gaacaactac aagaccacgc ctcccgtgct ggactccgac      840
ggctccttct cctctacag caagctcacc gtggacaaga gcaggtggca gcaggggaac      900
gtcttctcat gctccgtgat gcatgaggct ctgcacaacc actacacgca gaagagcctc      960
tccctgtctc cgggtaaatg a                                                981

<210> SEQ ID NO 70
<211> LENGTH: 384
<212> TYPE: DNA
<213> ORGANISM: Artificial Sequence
<220> FEATURE:
<223> OTHER INFORMATION: primer/sequence of interest

<400> SEQUENCE: 70
atggcctggg ctctgctgct cctcactctc ctcactcagg acacagggtc ctgggcctcc       60
tatgtgctga ctcagccgcc ctcagtgtct gcggccccag gcagaaggt caccatctcc      120 tgctctggag gcagctccaa catcgggaga tatcatgtat cgtggtacca gcagttccca      180
ggaacagccc ccaaactcat ctatggtgcc ggcaatcggc cctcagggt ccctgaccga      240 ttctctggct cccagtctgg cacctcaggc acgctgacca tcaatagact ccgtcctgag      300
gacgaggcga ttattactg ctcagcatgg gataggagcc tgaatgctct tttattcgga      360
ggagggaccc ggctgaccgt ccta                                             384

<210> SEQ ID NO 71
<211> LENGTH: 321
<212> TYPE: DNA
<213> ORGANISM: Artificial Sequence
<220> FEATURE:
<223> OTHER INFORMATION: primer/sequence of interest

<400> SEQUENCE: 71
ggtcagccca aggctgcccc ctcggtcact ctgttcccgc cctcctctga ggagcttcaa       60
gccaacaagg ccacactggt gtgtctcata agtgacttct acccgggagc cgtgacagtg      120
gcctggaagg cagatagcag ccccgtcaag gcggagtgg agaccaccac accctccaaa      180
caaagcaaca caagtacgc ggccagcagc tatctgagcc tgacgcctga gcagtggaag      240
tcccacagaa gctacagctg ccaggtcacg catgaaggga gcaccgtgga agagacagtg      300
gcccctacag aatgttcata g                                                321

<210> SEQ ID NO 72
<211> LENGTH: 405
<212> TYPE: DNA
<213> ORGANISM: Artificial Sequence
<220> FEATURE:
<223> OTHER INFORMATION: primer/sequence of interest

<400> SEQUENCE: 72
atggagtttg ggctgagctg gttttcctt gttgctattt taaaggtgt ccagtgtgag        60 gtgcagctgg tgcagtcctg ggctgaggtg aagaagcctg gggcctcagt gaagctctcc     120
tgcagggctt ccggttacac ttttaccagc gacagtataa attgggtgag acaggccct      180 ggacaaggac ttgagtggat gggatggatt aaccctagca atgggaatac aggctacgca     240
```

```
cagaagttcc agggcagagt caccatggcc agggacacgt ccacgaatac agcctacatg    300
gagctgagca gcctgacatc tgaggacacg gccgtatttt tctgtgcaag gggcgggaat    360
acagactact ggggccaggg ggtcctggtc accgtctcct cagct                    405
```

<210> SEQ ID NO 73
<211> LENGTH: 990
<212> TYPE: DNA
<213> ORGANISM: Artificial Sequence
<220> FEATURE:
<223> OTHER INFORMATION: primer/sequence of interest

<400> SEQUENCE: 73

```
agcaccaagg gcccatcggt cttccccctg gcaccctcct ccaagagcac ctctgggggc     60
acagcggccc tgggctgcct ggtcaaggac tacttccccg aaccggtgac ggtgtcgtgg    120
aactcaggcg ccctgaccag cggcgtgcac accttcccgg ctgtcctaca gtcctcagga    180
ctctactccc tcagcagcgt ggtgaccgtg ccctccagca gcttgggcac ccagacctac    240
atctgcaacg tgaatcacaa gcccagcaac accaaggtgg acaagaaagt tgagcccaaa    300
tcttgtgaca aaactcacac atgcccaccg tgcccagcac ctgaactcct ggggggaccg    360
tcagtcttcc tcttccccc aaaacccaag gacaccctca tgatctcccg gacccctgag    420
gtcacatgcg tggtggtgga cgtgagccac gaagaccctg aggtcaagtt caactggtac    480
gtggacggcg tggaggtgca taatgccaag acaaagccgc gggaggagca gtacaacagc    540
acgtaccgtg tggtcagcgt cctcaccgtc ctgcaccagg actggctgaa tggcaaggag    600
tacaagtgca aggtctccaa caaagccctc ccagccccca tcgagaaaac catctccaaa    660
gccaaagggc agccccgaga accacaggtg tacaccctgc ccccatcccg ggaggagatg    720
accaagaacc aggtcagcct gacctgcctg gtcaaaggct tctatcccag cgacatcgcc    780
gtggagtggg agagcaatgg gcagccggag aacaactaca agaccacgcc tcccgtgctg    840
gactccgacg gctccttctt cctctacagc aagctcaccg tggacaagag caggtggcag    900
caggggaacg tcttctcatg ctccgtgatg catgaggctc tgcacaacca ctacacgcag    960
aagagcctct ccctgtctcc gggtaaatga                                     990
```

<210> SEQ ID NO 74
<211> LENGTH: 384
<212> TYPE: DNA
<213> ORGANISM: Artificial Sequence
<220> FEATURE:
<223> OTHER INFORMATION: primer/sequence of interest

<400> SEQUENCE: 74

```
atggcctggg ctctgctgct cctcactctc ctcactcagg acacagggtc ctgggcctcc     60
tatgtgctga ctcagccacc ctcagtgtct gcggccccag gcagaggat catcatctcc    120 tgttctggaa gtagttccaa catcgggaga tattatgtat cctggtacca gcagttccca    180
ggaacagccc ccaaactcat ctatggttcc aacaatcgac cctcaggggt ccctgaccga    240
ttttctggct cccagtctgg cacctccgcc acgctgacca tcaatggact ccggcctgag    300
gacgaggcgg attattactg ctcagcatgg gatagaagcc tgaatgctct gttattcgga    360
ggagggaccc ggctcaccgt ccta                                           384
```

<210> SEQ ID NO 75
<211> LENGTH: 321
<212> TYPE: DNA

<213> ORGANISM: Artificial Sequence
<220> FEATURE:
<223> OTHER INFORMATION: primer/sequence of interest

<400> SEQUENCE: 75

| | | |
|---|---|---|
| ggtcagccca aggctgcccc ctcggtcact ctgttcccgc cctcctctga ggagcttcaa | 60 |
| gccaacaagg ccacactggt gtgtctcata agtgacttct acccgggagc cgtgacagtg | 120 |
| gcctggaagg cagatagcag ccccgtcaag gcgggagtgg agaccaccac accctccaaa | 180 |
| caaagcaaca caagtacgc ggccagcagc tatctgagcc tgacgcctga gcagtggaag | 240 |
| tcccacagaa gctacagctg ccaggtcacg catgaaggga gcaccgtgga agacagtg | 300 |
| gccctacag aatgttcata g | 321 |

<210> SEQ ID NO 76
<211> LENGTH: 432
<212> TYPE: DNA
<213> ORGANISM: Artificial Sequence
<220> FEATURE:
<223> OTHER INFORMATION: primer/sequence of interest

<400> SEQUENCE: 76

| | | |
|---|---|---|
| atggagtttg ggctgagctg ggttttcctt gttgctattt taaaggtgt ccagtgtcag | 60 |
| gtgcagctgg tgcagtccgg aggaggcttg gttcagccgg gggggtccct gagactctcc | 120 |
| tgtgcagcct ctggattcac tttcaggaat tatggcattc actgggtccg ccagtctcca | 180 |
| ggggagggac tggagtgggt gacatttatt tggtatgatg aagtctgaa atatttggca | 240 |
| gactctgtga agggccgatt caccatctcc agagacaatt ccaagaacat ggtttatctt | 300 |
| caaatgaaca acctgctatt ggggacacg ccgtatatt actgtgcgag gtcacgaatc | 360 |
| acactgattg gaccgcgtaa ttacggtctg gactcatggg gccaagggt cgtcgtcacc | 420 |
| gtctcctcag ct | 432 |

<210> SEQ ID NO 77
<211> LENGTH: 990
<212> TYPE: DNA
<213> ORGANISM: Artificial Sequence
<220> FEATURE:
<223> OTHER INFORMATION: primer/sequence of interest

<400> SEQUENCE: 77

| | | |
|---|---|---|
| agcaccaagg gcccatcggt cttccccctg gcaccctcct ccaagagcac ctctgggggc | 60 |
| acagcggccc tgggctgcct ggtcaaggac tacttcccg aaccggtgac ggtgtcgtgg | 120 |
| aactcaggcg ccctgaccag cggcgtgcac accttcccgg ctgtcctaca gtcctcagga | 180 |
| ctctactccc tcagcagcgt ggtgaccgtg ccctccagca gcttgggcac ccagacctac | 240 |
| atctgcaacg tgaatcacaa gcccagcaac accaaggtgg acaagaaagt tgagcccaaa | 300 |
| tcttgtgaca aaactcacac atgcccaccg tgcccagcac ctgaactcct ggggggaccg | 360 |
| tcagtcttcc tcttccccc aaaacccaag gacaccctca tgatctcccg gacccctgag | 420 |
| gtcacatgcg tggtggtgga cgtgagccac gaagaccctg aggtcaagtt caactggtac | 480 |
| gtggacggcg tggaggtgca taatgccaag acaaagccgc gggaggagca gtacaacagc | 540 |
| acgtaccgtg tggtcagcgt cctcaccgtc ctgcaccagg actggctgaa tggcaaggag | 600 |
| tacaagtgca aggtctccaa caaagccctc ccagccccca tcgagaaaac catctccaaa | 660 |
| gccaaagggc agccccgaga accacaggtg tacaccctgc ccccatcccg ggaggagatg | 720 |
| accaagaacc aggtcagcct gacctgcctg gtcaaaggct tctatccag cgacatcgcc | 780 |

| | |
|---|---|
| gtggagtggg agagcaatgg gcagccggag aacaactaca agaccacgcc tcccgtgctg | 840 |
| gactccgacg gctccttctt cctctacagc aagctcaccg tggacaagag caggtggcag | 900 |
| caggggaacg tcttctcatg ctccgtgatg catgaggctc tgcacaacca ctacacgcag | 960 |
| aagagcctct ccctgtctcc gggtaaatga | 990 |

<210> SEQ ID NO 78
<211> LENGTH: 387
<212> TYPE: DNA
<213> ORGANISM: Artificial Sequence
<220> FEATURE:
<223> OTHER INFORMATION: primer/sequence of interest

<400> SEQUENCE: 78

| | |
|---|---|
| atggcctggg ctctgctgct cctcactctc ctcactcagg acacagggtc ctgggcccag | 60 |
| tctgccctga ctcagccacc ctcagcgtct ggggcccccg ggcagagtgc caccattacc | 120 |
| tgttctggaa gcagctccaa catcggaaat aattacgttt attggtacca acaagtctcc | 180 |
| ggaaaggccc ccaaactcct catctataat gataatctga cccacagg ggtccctgct | 240 |
| cggttttctg gctccaagtc tggcacgtca gcctccctgg ccatcactgg gctccagtcc | 300 |
| gaggatgagg ctgattatta ctgctcaaca tgggatcgcg gcctggacgg tttgttattc | 360 |
| ggtggaggga cccggctcac cgtccta | 387 |

<210> SEQ ID NO 79
<211> LENGTH: 321
<212> TYPE: DNA
<213> ORGANISM: Artificial Sequence
<220> FEATURE:
<223> OTHER INFORMATION: primer/sequence of interest

<400> SEQUENCE: 79

| | |
|---|---|
| ggtcagccca aggctgcccc ctcggtcact ctgttcccgc cctcctctga ggagcttcaa | 60 |
| gccaacaagg ccacactggt gtgtctcata agtgacttct acccgggagc cgtgacagtg | 120 |
| gcctggaagg cagatagcag ccccgtcaag gcgggagtgg agaccaccac accctccaaa | 180 |
| caaagcaaca acaagtacgc ggccagcagc tatctgagcc tgacgcctga gcagtggaag | 240 |
| tcccacagaa gctacagctg ccaggtcacg catgaaggga gcaccgtgga agacagtg | 300 |
| gccccctacag aatgttcata g | 321 |

<210> SEQ ID NO 80
<211> LENGTH: 423
<212> TYPE: DNA
<213> ORGANISM: Artificial Sequence
<220> FEATURE:
<223> OTHER INFORMATION: primer/sequence of interest
<220> FEATURE:
<221> NAME/KEY: misc_feature
<222> LOCATION: 387..387
<223> OTHER INFORMATION: /note="n is a, c, g, or t"

<400> SEQUENCE: 80

| | |
|---|---|
| atggagtttg ggctgagctg ggttttcctt gttgctattt taaaaggtgt ccagtgtgag | 60 |
| gtgcagctgt tgcagtctgg cccaggactg gtgaaggctt cggagaccct gtccctcacc | 120 |
| tgcgctgtct ctggtggctc catcagcagt aattatggct ggagctggat ccgccagccc | 180 |
| ccagggaagg ggctggagtg gattgcatat atcggtggta gtagtggtaa caccaactac | 240 |
| aacccctccc tcaagagtcg agtcactatt tcaaaagaca cgtccaagaa ccagttctcc | 300 |

| | |
|---|---|
| ctgaagctga cctctgtgac cgccgcggac acggccattt attactgtgc gagatataaa | 360 |
| acggagggag cgacacggtt tgagtantgg agccagggag tcctggtcac cgtctcctca | 420 |
| gct | 423 |

<210> SEQ ID NO 81
<211> LENGTH: 990
<212> TYPE: DNA
<213> ORGANISM: Artificial Sequence
<220> FEATURE:
<223> OTHER INFORMATION: primer/sequence of interest

<400> SEQUENCE: 81

| | |
|---|---|
| agcaccaagg gcccatcggt cttccccctg gcaccctcct ccaagagcac ctctgggggc | 60 |
| acagcggccc tgggctgcct ggtcaaggac tacttccccg aaccggtgac ggtgtcgtgg | 120 |
| aactcaggcg ccctgaccag cggcgtgcac accttcccgg ctgtcctaca gtcctcagga | 180 |
| ctctactccc tcagcagcgt ggtgaccgtg ccctccagca gcttgggcac ccagacctac | 240 |
| atctgcaacg tgaatcacaa gcccagcaac accaaggtgg acaagaaagt tgagcccaaa | 300 |
| tcttgtgaca aaactcacac atgcccaccg tgcccagcac ctgaactcct ggggggaccg | 360 |
| tcagtcttcc tcttcccccc aaaacccaag gacaccctca tgatctcccg gacccctgag | 420 |
| gtcacatgcg tggtggtgga cgtgagccac gaagaccctg aggtcaagtt caactggtac | 480 |
| gtggacggcg tggaggtgca taatgccaag acaaagccgc gggaggagca gtacaacagc | 540 |
| acgtaccgtg tggtcagcgt cctcaccgtc ctgcaccagg actggctgaa tggcaaggag | 600 |
| tacaagtgca aggtctccaa caaagccctc ccagccccca tcgagaaaac catctccaaa | 660 |
| gccaaagggc agccccgaga accacaggtg tacaccctgc ccccatcccg ggaggagatg | 720 |
| accaagaacc aggtcagcct gacctgcctg gtcaaaggct tctatcccag cgacatcgcc | 780 |
| gtggagtggg agagcaatgg gcagccggag aacaactaca agaccacgcc tcccgtgctg | 840 |
| gactccgacg gctccttctt cctctacagc aagctcaccg tggacaagag caggtggcag | 900 |
| caggggaacg tcttctcatg ctccgtgatg catgaggctc tgcacaacca ctacacgcag | 960 |
| aagagcctct ccctgtctcc gggtaaatga | 990 |

<210> SEQ ID NO 82
<211> LENGTH: 387
<212> TYPE: DNA
<213> ORGANISM: Artificial Sequence
<220> FEATURE:
<223> OTHER INFORMATION: primer/sequence of interest

<400> SEQUENCE: 82

| | |
|---|---|
| atggcctggg ctctgctgct cctcactctc ctcactcagg acacagggtc ctgggcctcc | 60 |
| tatgtgctga ctcagccacc ctcagcgtct gaggccgcca ggaagagtgt caccacctcc | 120 |
| tgttctggaa gcacctccaa catcggaagt aatagtgtat cctggtacca gcagctccca | 180 |
| ggaacagctc ccaaactcct catctattat aatgatcaac gagcctcagg tgtctctgac | 240 |
| cgattctctg cctccaagac tggcacgtca gcctccctgg ccatcagtgg gctccagacc | 300 |
| gaggatgagg ctgattatta ctgcgcagca tgggatgata gcctgagcgg tccgttattc | 360 |
| ggaggaggga cccggctgac cgtccta | 387 |

<210> SEQ ID NO 83
<211> LENGTH: 321
<212> TYPE: DNA
<213> ORGANISM: Artificial Sequence
<220> FEATURE:
<223> OTHER INFORMATION: primer/sequence of interest

<400> SEQUENCE: 83

```
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca caagtacgc ggccagcagc tatctgagcc tgacgcctga gcagtggaag    240
tcccacagaa gctacagctg ccaggtcacg catgaaggga gcaccgtgga aagacagtg    300 gcccctacag aatgttcata g                                             321
```

<210> SEQ ID NO 84
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 84

```
Leu Ile Gly Leu Arg Ile Ile Phe Ala Val Leu Ser Ile Val Asn
1               5                   10                  15
```

<210> SEQ ID NO 85
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 85

```
Arg Ile Ile Phe Ala Val Leu Ser Ile Val Asn Arg Val Arg Gln
1               5                   10                  15
```

<210> SEQ ID NO 86
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 86

```
Ala Val Leu Ser Ile Val Asn Arg Val Arg Gln Gly Tyr Ser Pro
1               5                   10                  15
```

<210> SEQ ID NO 87
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 87

```
Ile Val Asn Arg Val Arg Gln Gly Tyr Ser Pro Leu Ser Phe Gln
1               5                   10                  15
```

<210> SEQ ID NO 88
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 88

Val Arg Gln Gly Tyr Ser Pro Leu Ser Phe Gln Thr Leu Thr Pro
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 89

Tyr Ser Pro Leu Ser Phe Gln Thr Leu Thr Pro Asn Pro Arg Gly
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 90

Ser Phe Gln Thr Leu Thr Pro Asn Pro Arg Gly Pro Asp Arg Leu
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 91

Leu Thr Pro Asn Pro Arg Gly Pro Asp Arg Leu Gly Arg Ile Glu
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 92

Pro Arg Gly Pro Asp Arg Leu Gly Arg Ile Glu Glu Glu Gly Gly
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 93

Asp Arg Leu Gly Arg Ile Glu Glu Glu Gly Gly Glu Gln Asp Arg
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 94

Arg Ile Glu Glu Glu Gly Gly Glu Gln Asp Arg Asp Arg Ser Ile

-continued

```
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: primer/sequence of interest

<400> SEQUENCE: 95

Glu Gly Gly Glu Gln Asp Arg Asp Arg Ser Ile Arg Leu Val Asn
1               5                   10                  15

<210> SEQ ID NO 96
<211> LENGTH: 59
<212> TYPE: PRT
<213> ORGANISM: Artificial Sequence
<220> FEATURE:
<223> OTHER INFORMATION: primer/sequence of interest

<400> SEQUENCE: 96

Leu Ile Gly Leu Arg Ile Ile Phe Ala Val Leu Ser Ile Val Asn Arg
1               5                   10                  15

Val Arg Gln Gly Tyr Ser Pro Leu Ser Phe Gln Thr Leu Thr Pro Asn
            20                  25                  30

Pro Arg Gly Pro Asp Arg Leu Gly Arg Ile Glu Glu Glu Gly Gly Glu
        35                  40                  45

Gln Asp Arg Asp Arg Ser Ile Arg Leu Val Asn
    50                  55

<210> SEQ ID NO 97
<211> LENGTH: 27
<212> TYPE: PRT
<213> ORGANISM: Artificial Sequence
<220> FEATURE:
<223> OTHER INFORMATION: primer/part of sequence of interest

<400> SEQUENCE: 97

Pro Asn Pro Arg Gly Pro Asp Arg Leu Gly Arg Ile Glu Glu Glu Gly
1               5                   10                  15

Gly Glu Gln Asp Arg Asp Arg Ser Ile Arg Val
            20                  25

<210> SEQ ID NO 98
<211> LENGTH: 18
<212> TYPE: PRT
<213> ORGANISM: Artificial Sequence
<220> FEATURE:
<223> OTHER INFORMATION: primer/part of sequence of interest

<400> SEQUENCE: 98

Cys Pro Asn Pro Arg Gly Pro Asp Arg Leu Gly Arg Ile Glu Glu Glu
1               5                   10                  15

Gly Gly
```

RECOMBINANT HIV EPITOPES AND USES THEREOF

CROSS REFERENCE TO RELATED APPLICATIONS

This application claims the benefit of and priority to PCT/US2017/060342, filed on Nov. 7, 2017, entitled, "NOVEL RECOMBINANT HIV EPITOPES AND USES THEREOF," which claims the benefit of and priority to U.S. Provisional Application No. 62/418,729, filed on Nov. 7, 2016, which are hereby incorporated by reference in their entirety.

GOVERNMENT SUPPORT

This invention was made with government support under Grant Nos. P01 AI048240 and R01 AI100703 awarded by the National Institutes of Health. The government has certain rights in the invention.

TECHNICAL FIELD

The present disclosure relates to certain epitopes in the C-terminal domain of the HIV-1 gp41 protein, and more specifically to compositions and methods for using the epitopes to develop vaccine protection against HIV.

BACKGROUND

The envelope protein of human immunodeficiency virus (HIV) is synthesized as a gp160 polypeptide, and is cleaved by a cellular protease to yield a non-covalently linked heterodimer—an external gp120 domain and a transmembrane, anchoring gp41 domain. The gp41 protein can be structurally sub-divided into three major domains: the extracellular domain (or ectodomain), the membrane-spanning domain, and the C-terminal tail (CTT). The CTT of gp41 protein has not received much attention as the target for the development of HIV vaccine. Efforts to design immunogens capable of presenting neutralizing epitopes targeting the CTT of gp41 are still largely unsuccessful.

SUMMARY

There is a need for broadly neutralizing monoclonal antibodies (mAbs) that target the CTT and can provide protection from the HIV virus. Disclosed herein are compositions and methods that address the shortcomings of the art, and may provide any number of additional or alternative advantages.

The present disclosure relates to anti-HIV antibodies that have been linked to vaccine-induced protection and that interact with conformational epitopes derived from the CTT of gp41 of HIV-1. Embodiments of the disclosure include recombinant nucleic acid compositions containing sequences having 80% or more identity to nucleic acid sequence of the Kennedy Loop, which is a segment of peptides in the CTT. Embodiments of the disclosure include recombinant nucleic acid compositions containing sequences having 90% or more identity to nucleic acid sequence of the Kennedy Loop of gp41. Embodiments of the disclosure include polypeptide compositions containing amino acid sequences having 80% or more identity to amino acid sequence corresponding to the Kennedy Loop of gp41 and are conformationally constrained by the addition of cysteine sequences. Embodiments of the disclosure include polypeptide compositions containing amino acid sequences having 90% or more identity to amino acid sequence corresponding to the Kennedy Loop of gp41 and are conformationally constrained by the addition of cysteine sequences.

Embodiments include vaccine compositions effective against a Human Immunodeficiency Virus-1 (HIV-1) infection and containing a recombinant peptide sequence that has at least 90% or more sequence identity to C-terminal domain of Kennedy loop of a HIV-1 gp41 protein and is conformationally constrained by a two or more cysteine residues. Embodiments include vaccine compositions effective against a Human Immunodeficiency Virus-1 (HIV-1) infection and containing a recombinant peptide sequence that has at least 90% or more sequence identity to N-terminal domain of Kennedy loop of a HIV-1 gp41 protein and is conformationally constrained by a two or more cysteine residues. In certain embodiments, the cysteine residues are the terminal residues of the recombinant peptide sequence.

Embodiments of the disclosure include isolated HIV monoclonal antibodies comprising an antibody binding portion that interacts with a polypeptide with an amino acid sequence 90% or more identical to an amino acid sequence corresponding to the Kennedy Loop of gp41 and is conformationally constrained by the addition of cysteine sequences. Embodiments include monoclonal antibody compositions capable of specifically binding to a recombinant peptide sequence that has at least 90% or more sequence identity to C-terminal domain of Kennedy loop of a HIV-1 gp41 protein and is conformationally constrained by a two or more cysteine residues. Embodiments include monoclonal antibody compositions capable of specifically binding to a recombinant peptide sequence that has at least 90% or more sequence identity to N-terminal domain of Kennedy loop of a HIV-1 gp41 protein and is conformationally constrained by a two or more cysteine residues. Embodiments include monoclonal antibody compositions capable of specifically binding to C-terminal domain of the HIV-1 gp41 protein and containing a heavy chain with a variable region having at least 80% or more sequence identity to the 61p1B2 variable heavy sequence and a light chain with a variable region having at least 80% or more sequence identity to the 61p1B2 variable light chain sequence.

Numerous other aspects, features and benefits of the present disclosure may be made apparent from the following detailed description taken together with the drawing figures. The pharmaceutical compositions can include compositions described herein, other components, or ingredients depending on desired prevention and treatment goals. It should be further understood that both the foregoing general description and the following detailed description are exemplary and explanatory and are intended to provide further explanation of the disclosure as claimed.

BRIEF DESCRIPTION OF THE DRAWINGS

The present disclosure can be better understood by referring to the following figures. The components in the figures are not necessarily to scale. The emphasis is instead placed upon illustrating the principles of the disclosure. In the figures, reference numerals designate corresponding parts throughout the different views.

FIG. 2 is a Mega alignment of the Kennedy Loop region sequences of HIV-1.

FIG. 4 is a listing of the DNA and amino acid sequences of the different domains of the Kennedy Loop region—Kennedy Loop N-terminal region with cysteine from the HIV-1 consensus sequence, Kennedy Loop C-terminal region with cysteine from the HIV-1 consensus sequence, and the epitope for SAR-1 monoclonal antibody with cysteine from the HIV-1 consensus sequence according to an exemplary embodiment.

FIG. 5 is a listing of the scrambled DNA and amino acid sequences corresponding to the different domains of the Kennedy Loop region described in FIG. 4, according to an exemplary embodiment.

FIGS. 9A-9C are graphical representations of plasma reactivity to the scrambled Kennedy loop-GFP recombinant fusion proteins: Scram-K-CTcc, Scram-K-NTcc, Scram-K-SARcc, respectively, where the plasma for each of the assays was obtained from vaccine-protected animals, according to an exemplary embodiment.

FIG. 14 is a representation of the yield of anti-Kennedy loop monoclonal antibodies from single B cells, according to an exemplary embodiment.

FIG. 15 is the sequence listing of the variable heavy (VH) chain gene sequence and the constant heavy (CH) chain gene sequences of mAb 61p1B2.

FIG. 16 is the sequence listing of the variable light (VL) chain gene sequence and the constant light (CL) chain gene sequences of mAb 61p1B2.

FIG. 17 is the sequence listing of the variable heavy (VH) chain gene sequence and the constant heavy (CH) chain gene sequences of mAb 61p1C5.

FIG. 18 is the sequence listing of the variable light (VL) chain gene sequence and the constant light (CL) chain gene sequences of mAb 61p1C5.

FIG. 19 is the sequence listing of the variable heavy (VH) chain gene sequence and the constant heavy (CH) chain gene sequences of mAb 61p1E2.

FIG. 20 is the sequence listing of the variable light (VL) chain gene sequence and the constant light (CL) chain gene sequences of mAb 61p1E2.

FIG. 21 is the sequence listing of the variable heavy (VH) chain gene sequence and the constant heavy (CH) chain gene sequences of mAb 61p1F4.

FIG. 22 is the sequence listing of the variable light (VL) chain gene sequence and the constant light (CL) chain gene sequences of mAb 61p1F4.

FIG. 23 is the sequence listing of the variable heavy (VH) chain gene sequence and the constant heavy (CH) chain gene sequences of mAb 61p1D3.

FIG. 24 is the sequence listing of the variable light (VL) chain gene sequence and the constant light (CL) chain gene sequences of mAb 61p1D3.

FIG. 26 is a schematic representation of the epitope mapping of the anti-Kennedy loop monoclonal antibodies, according to an exemplary embodiment.

DETAILED DESCRIPTION

Figure 1:
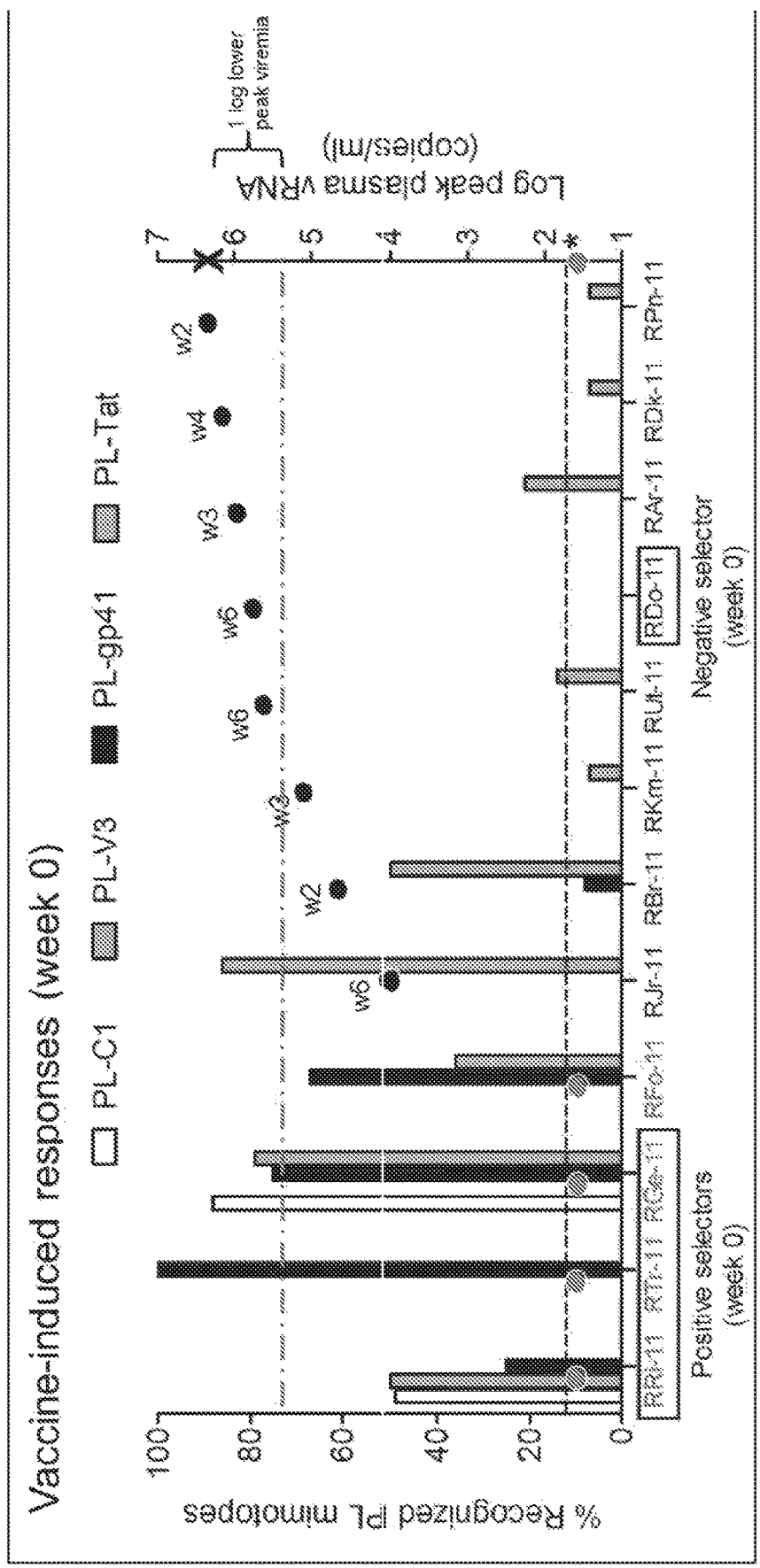
FIG. 1 is a graphical representation of the reactivity of the rhesus monkey plasma against a panel of protection-linked mimotopes, according to an exemplary embodiment.

Reference will now be made to the exemplary embodiments illustrated in the drawings, and specific language will be used here to describe the same. It will nevertheless be understood that no limitation of the scope of the disclosure is thereby intended. Alterations and further modifications of the inventive features illustrated here, and additional applications of the principles of the disclosures as illustrated here, which would occur to one skilled in the relevant art and having possession of this disclosure, are to be considered within the scope of the disclosure.

The disclosure provides methods, compositions and kits for preventing an HIV infection. For example, HIV envelope-like polypeptides (wild-type HIV polypeptides and mimotopes) may be administered to an individual so as to induce a protective immune response to HIV. Alternatively, antibodies directed to the HIV envelope-like polypeptides may be administered to an individual to treat or prevent an HIV infection and/or one or more symptoms associated with the infection (e.g., AIDS).

As used here, the following terms may have the following definitions:

The term "HIV" is meant to include different form of the Human Immunodeficiency Virus, such as HIV-1 and HIV-2 and also the simian immunodeficiency virus (SIV). HIV is organized into groups and subtypes (clades).

The terms "env polypeptide" or "envelope polypeptide" refer to a molecule derived from an HIV envelope protein. The envelope protein of HIV is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of the virion, while the gp120 segment protrudes into the surrounding environment. env polypeptides can exist as monomers, dimers or multimers.

As used herein, the term "vaccine(s)" or "vaccine composition" means a recombinant product, the administration of which is intended to elicit an immune response(s) that can prevent and/or lessen the severity of one or more infectious diseases.

As used herein, a "mimotope" is a polypeptide, which differs from an envelope polypeptide by one or more amino acids but which mimics the three dimensional structure of a wild-type envelope epitope. A mimotope generally in the context of a larger protein backbone called carrier is able to stimulate a host's immune system to produce an antibody antigen-specific response. The host generates antibodies that specifically bind to the mimotope and the corresponding wild-type envelope epitope.

As used herein, "antigen" refers to a molecule containing one or more epitopes/mimotope (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. Antigens of the present disclosure include the polypeptides of FIGS. 2 and 4. As used herein, an "antibody" includes any reactive fragment or fragments of antibodies such as Fab molecules, Fab proteins, single chain polypeptides, or the multi-functional antibodies having binding affinity for an antigen. The term includes chimeric antibodies, altered antibodies, univalent antibodies, bi-specific antibodies, monoclonal antibodies, polyclonal antibodies, human antibodies and humanized antibodies. Methods for preparing antibodies are well known in the art and described herein. A "neutralizing antibody" is an antibody that prevents HIV infection of target cells.

The term "specifically binds" or "specifically binding" means a high avidity and/or high affinity binding of an antibody to a specific antigen (e.g., the Kennedy loop or fragments thereof). Antibody binding to its epitope on this specific antigen is stronger than binding of the same antibody to any other epitope, particularly those which may be present in molecules in association with, or in the same sample, as the specific antigen of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present disclosure to prevent the onset of the symptoms or complications, alleviate the symptoms or complications, or eliminate the disease, condition, or disorder. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Illustratively, an effective amount of the compositions of this disclosure ranges from nanogram/kg to milligram/kg amounts of the compositions alone or in combination with other compounds for young children and adults. Equivalent dosages for lighter or heavier body weights can readily be determined. The dose should be adjusted to suit the individual to whom the composition is administered and will vary with age, weight and metabolism of the individual. The exact amount of the composition required will vary from subject to subject, depending on the species, age, weight and general condition of the subject, the particular peptide or polypeptide used, its mode of administration and the like. An appropriate amount can be determined by one of ordinary skill in the art using only routine experimentation given the teachings herein. One skilled in the art will realize that dosages are best optimized by the practicing physician or veterinarian and methods for determining dose amounts and regimens.

The compositions herein are formulated in accordance to the mode of potential administration. Thus, if the composition is intended to be administered intranasally or by inhalation, for example, the composition may be a converted to a powder or aerosol form, as conventional in the art, for such purposes. Other formulations, such as for oral or parenteral delivery, are also used as conventional in the art. Compositions for administration herein may form solutions, suspensions, tablets, pills, capsules, sustained release formulations or powders.

Optimal dosages to be administered may be readily determined by those skilled in the art, and will vary with the particular compound used, the mode of administration, the strength of the preparation, the mode of administration, the number of consecutive administrations within a limited period of time (e.g. up to 60 minutes) and the advancement of the disease condition. In addition, factors associated with the particular patient being treated, including patient age, weight, diet and time of administration, will result in the need to adjust dosages. The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The following Examples are set forth to aid in the understanding of the disclosure, and are not intended and should not be construed to limit in any way the disclosure set forth in the claims which follow thereafter.

Design and Construction of Epitope

Six rhesus monkeys (RMs) from a vaccine study were found to be protected from virus challenges after vaccination either completely or partially, the latter being defined as 1 log lower peak viremia compared to the mean viremia of the unvaccinated controls (one rhesus monkey had borderline protection, and five had clear vaccine failure during the first five low-dose challenges with a heterologous simian-human immunodeficiency virus (SHIV), i.e., a virus with an HIV-1 envelope that differed from the HIV-1 envelope given as an immunogen in the form of trimeric gp160 (FIG. 1). The rhesus monkeys had been vaccinated with recombinant proteins (SIV Gag-Pol particles, HIV-1 Tat and trimeric HIV-1 gp160 in incomplete Freund's adjuvant). Among the protected vaccine recipient rhesus monkeys, five rhesus monkeys (including rhesus monkeys #RRi-11 and #RTr-11) had antibody (Ab) responses against the Kennedy Loop region of HIV-1 gp41 (black bars, FIG. 1). This response was absent in unvaccinated infected control rhesus monkeys or in vaccinated rhesus monkeys with vaccine failure. This makes the Kennedy Loop a strong humoral correlate of protection.

FIG. 1 shows the reactivity of the rhesus monkey plasma against a panel of protection-linked (PL) mimotopes. The vaccine-induced responses targeting gp41 (black bars in FIG. 1) were only observed in vaccine-protected rhesus monkeys. Those against gp41 were mapped to a region on the intracellular tail of gp41, the Kennedy Loop region. The PL-mimotopes had been selected as previously described (Bachler et al., J Virol 2013). In the first phase of SHIV challenges, all rhesus monkeys received 5 low-dose intrarectal challenges. Rhesus monkeys that remained aviremic after the 5th challenge (RRi-11, RTr-11, RGe-11, and RFo-11 as well as one out of the 17 non-vaccinated controls (red dot with an asterisk on the right y axis)) were assigned a vRNA load of 49 copies/ml (red dots below the black dashed line that indicates the sensitivity of the vRNA load test by RT-PCR (50 copies/ml)). All five animals later received a high-dose SHIV virus re-challenge, after which the control rhesus monkey a well as RGe-11 and RFo-11 became viremic. X indicates the mean peak plasma viremia of unvaccinated controls; black dots indicate the peak plasma viral RNA load (vRNA); the w above black dots indicate the number of weeks post-inoculation at which peak viremia occurred. The red horizontal dashed line indicates 1 log lower than the mean peak viremia (X) of the unvaccinated controls. This value was used as cut-off for partial protection in vaccinated animals with breakthrough infection. The 12 vaccinated animals were ranked from left to right in the order of progressively lower degrees of protection (increasing peak vRNA loads occurring at earlier week post-first challenge.

Figure 3:
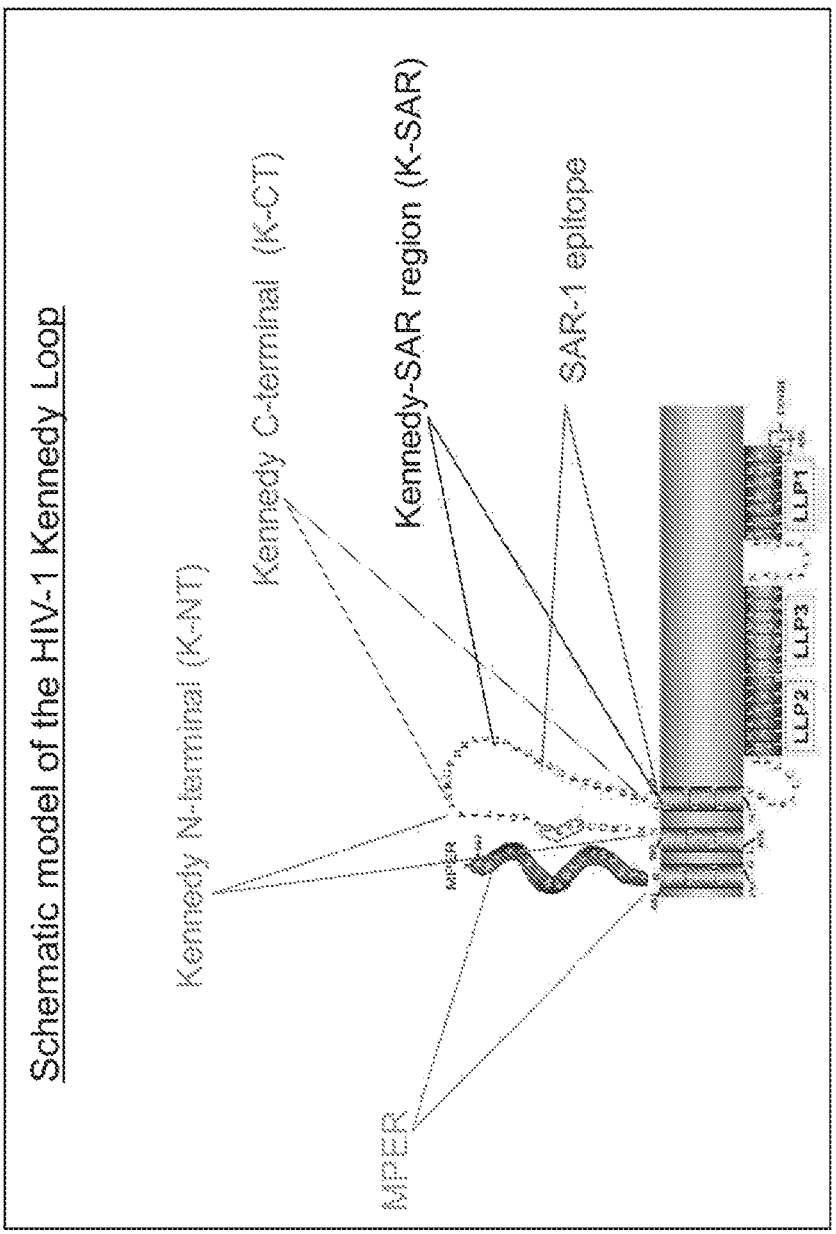
FIG. 3 is a diagrammatic representation of the HIV-1 Kennedy Loop and membrane-proximal external domain of gp41.

The Kennedy Loop region of gp41 was designed and constructed as a novel constrained loop, linked to green fluorescent protein (GFP) and was used as a bait to isolate B cells specific to the Kennedy Loop. The entire Kennedy Loop of 40 amino acids was used to generate cysteine-constrained loops of sub-regions thereof (See FIGS. 2 and 3). This 40-amino acid region is substantially conserved across different clades. The Kennedy loop protein or fragments thereof were expressed, purified and tested for their efficacy and specificity in the form of fusion proteins with green fluorescent protein (GFP). Epitope-specific monoclonal antibodies were isolated against the Kennedy Loop of the gp41 region. For cloning purposes, this 40 amino acid Kennedy Loop region was split into 3 domains, namely the Kennedy N-terminal (K-NT) domain; the Kennedy C-terminal (K-CT) domain, and the segment where the epitope for anti-Kennedy-loop mouse mAb SAR-1 (K-SAR) is located (FIG. 3). FIG. 4 is a listing of the DNA and amino acid sequences of the different domains of the Kennedy Loop region Kennedy Loop N-terminal region with cysteine from the HIV-1 consensus sequence, Kennedy Loop C-terminal region with cysteine from the HIV-1 consensus sequence, and the epitope for SAR-1 monoclonal antibody with cysteine from the HIV-1 consensus sequence.

Figure 6:
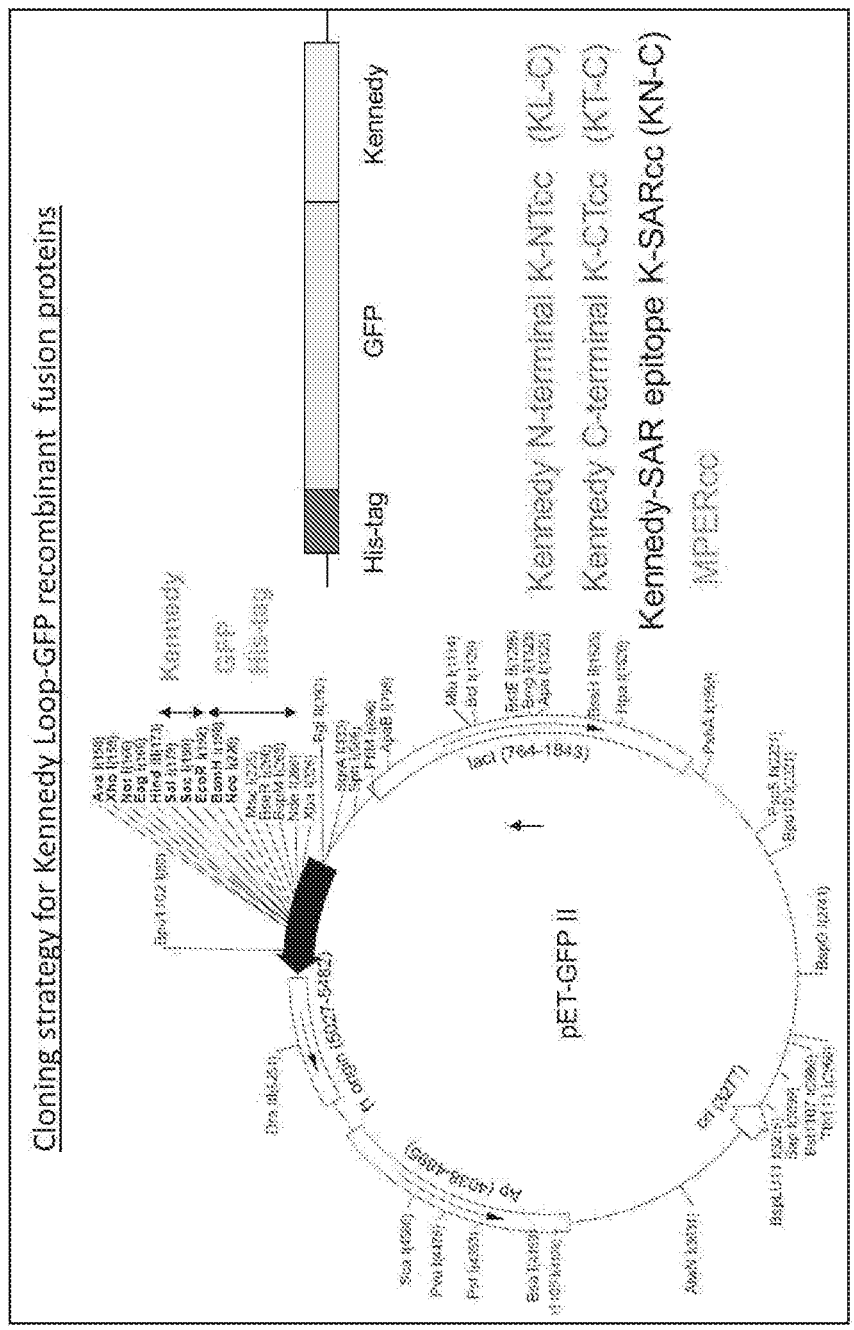
FIG. 6 is a diagrammatic representation of the cloning strategy for Kennedy Loop-GFP recombinant fusion proteins.
Figures 7A, 7B:
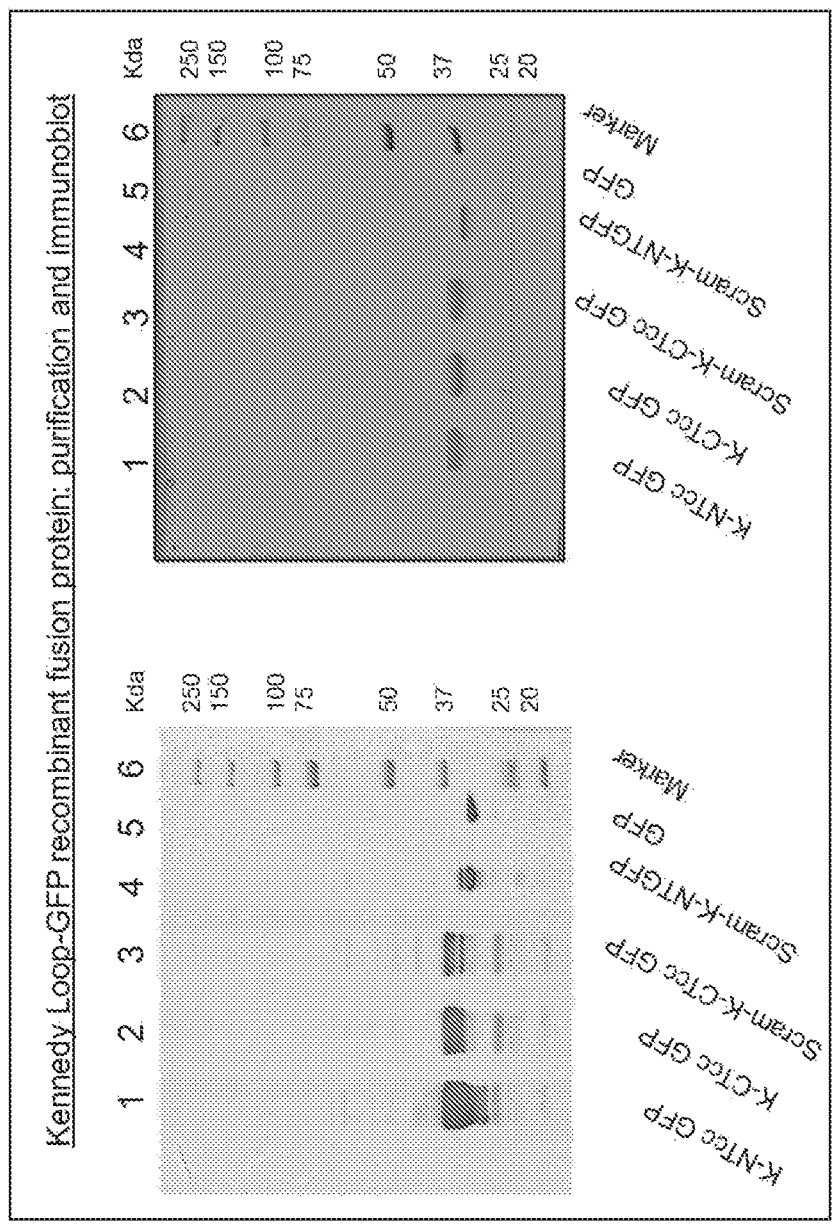
FIGS. 7A and 7B are images of an acrylamide gel showing the purification of the recombinant proteins and an immunoblot confirming expression of the Kennedy Loop-GFP recombinant fusion proteins in a bacterial expression system.

Analysis of the protein sequences of the Kennedy Loop for structural stability and hydrophobicity index showed that the Kennedy Loop is very flexible and may not retain any structure. Keeping this in mind, two cysteine amino acids were synthesized at the ends of all the sequences to create novel constrained and structurally stable epitope loops. DNA sequences were synthesized after codon optimization for recombinant expression in E. coli. The DNA and amino acid sequences, as shown in FIG. 4, for each domain were designed and synthesized. As experimental controls, scrambled DNA sequences for each domain were designed and synthesized. The DNA and amino acid sequences for each scrambled domain are shown in FIG. 5. The DNA sequences were ligated and cloned in an in-house modified recombinant expression vector that contains mWasabi, a type of GFP and a 6-histidine tag (His-tag). Restriction cloning was done at the C-terminal of the GFP sequence as shown in FIG. 6. The recombinant plasmids were transformed in BL-21 competent cells. Single colony bacterial cultures were induced with Isopropyl β-D-1-thiogalactopyranoside (IPTG) to express Kennedy Loop-GFP and scrambled peptide of Kennedy Loop-GFP recombinant fusion proteins. The latter were purified on a commercial Ni-NTA chromatography column and tested for its expression and purification, as shown on the SDS PAGE in FIG. 7A. The proteins were detected by anti-histidine antibodies by immunoblot, as shown by the Western Blot image in FIG. 7B.

Figure 8:
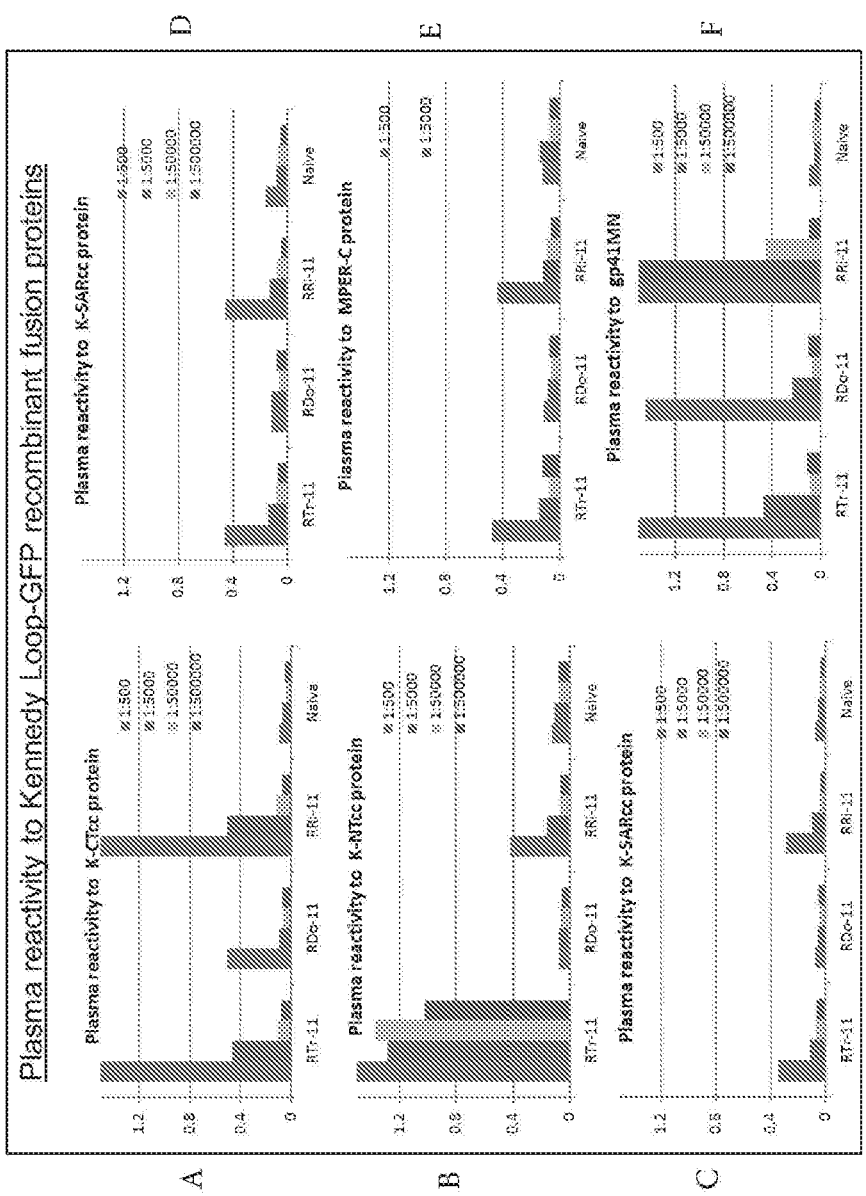
FIGS. 8A-8F are graphical representations of plasma reactivity to the Kennedy loop-GFP recombinant fusion proteins: K-CTcc, K-NTcc, K-SARcc, K-SARcc, MPER-C, and gp41MN, respectively, and the plasma for each of the assays was obtained from vaccine-protected animals, according to an exemplary embodiment.
Figure 9:
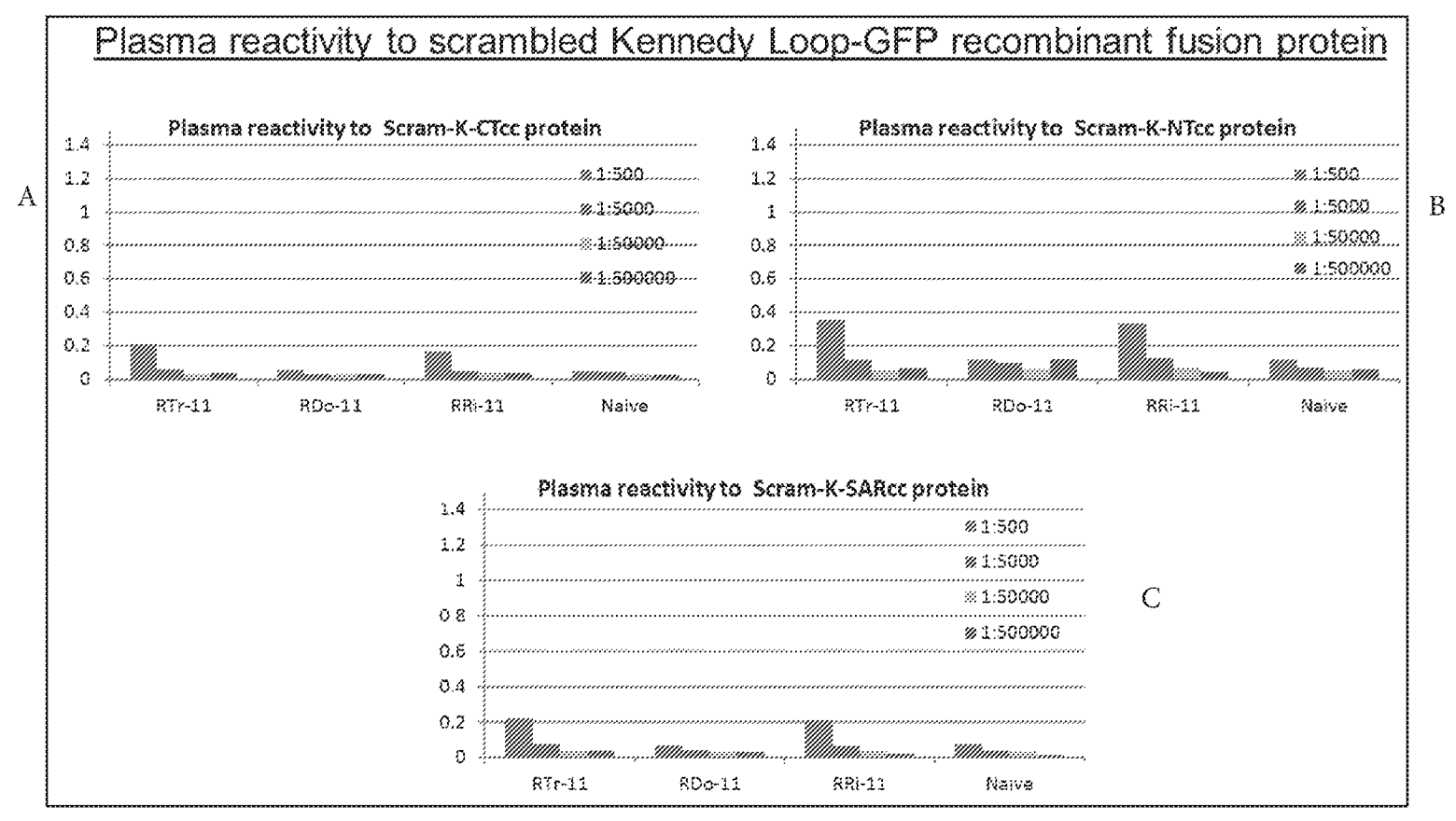

The Kennedy Loop-GFP recombinant fusion proteins and scrambled Kennedy Loop-GFP recombinant fusion proteins were tested for their binding specificity to sera of rhesus monkeys #RTr-11 and #RRi-11 (vaccine-protected monkeys) as well as to rhesus monkey #RDo-11 (vaccinated rhesus monkey with vaccine failure; please see black boxed rhesus monkey in FIG. 1. Serum from this rhesus monkey had been used in the negative counter-selection for isolating PL mimotopes as previously described in Bachler et al., J Virol 2013, as shown in FIGS. 8 & 9. FIGS. 8A-8F are graphical representations of plasma reactivity to the Kennedy Loop-GFP recombinant fusion proteins: K-CTcc, K-NTcc, K-SARcc, K-SARcc, MPER-C, and gp41MN, respectively, and the plasma for each of the assays was obtained from vaccine-protected animals. These graphs show the dose-dependent specific binding of the Kennedy Loop-GFP recombinant fusion protein to plasma from vaccine-protected rhesus monkeys (RTr-11 and RRi-11). Minimal to no reactivity was observed with plasma samples from naïve rhesus monkey and the viremic rhesus monkey with vaccine failure (RDo-11). All the tests were done in triplicates using ELISA. FIGS. 9A-9C are graphical representations of plasma reactivity to the scrambled Kennedy loop-GFP recombinant fusion proteins: Scram-K-CTcc, Scram-K-NTcc, Scram-K-SARcc, respectively, where the plasma for each of the assays was obtained from vaccine-protected animals, according to an exemplary embodiment. These graphs show the lack of binding or non-reactivity of scrambled Kennedy Loop-GFP recombinant fusion protein. No significant reactivity was observed by any of the rhesus monkey plasma samples tested on the scrambled recombinant fusion proteins. All the tests were done in triplicates using ELISA.

Figure 10:
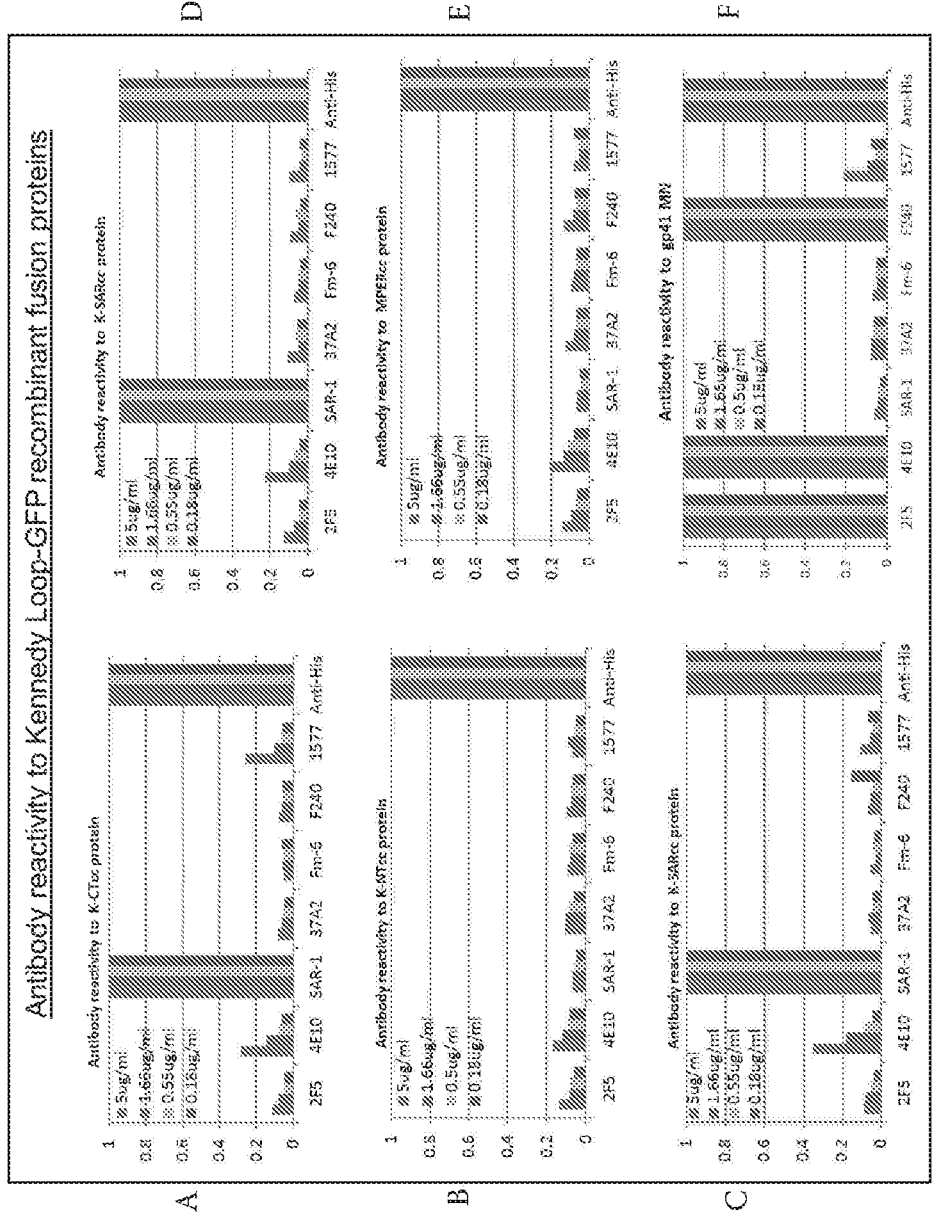
FIGS. 10A-10F are graphical representations of antibody reactivity to the Kennedy loop-GFP recombinant fusion proteins: K-CTcc, K-NTcc, K-SARcc, K-SARcc, MPER-C, and gp41MN, respectively, using a panel of known anti-HIV-1 envelope monoclonal antibodies, according to an exemplary embodiment.
Figure 11:
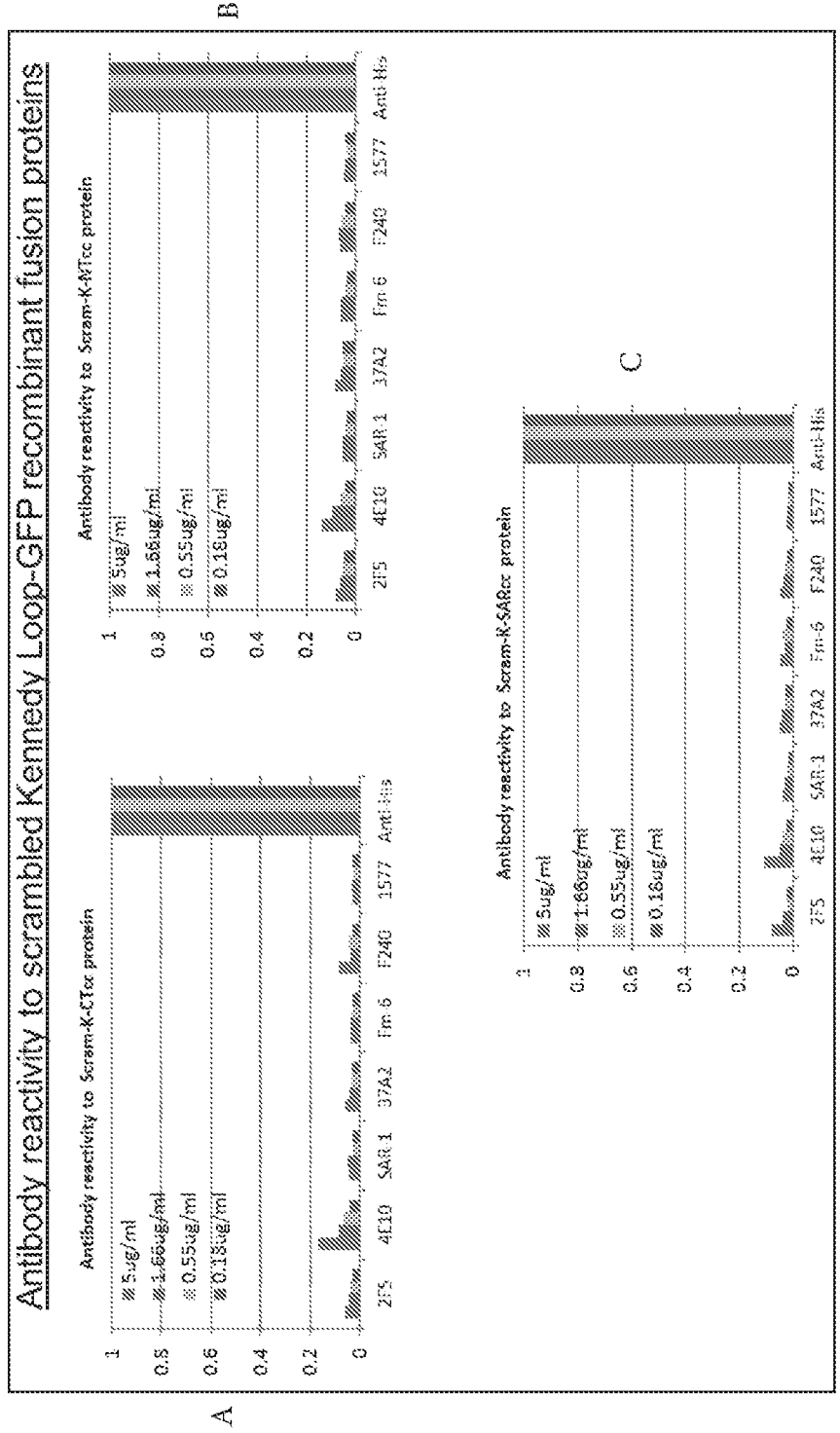
FIGS. 11A-11C are graphical representations of antibody reactivity to the scrambled Kennedy loop-GFP recombinant fusion proteins: Scram-K-CTcc, Scram-K-NTcc, Scram-K-SARcc, respectively, using a panel of known anti-HIV-1 envelope monoclonal antibodies, according to an exemplary embodiment.

The Kennedy Loop-GFP recombinant fusion proteins and scrambled Kennedy Loop-GFP recombinant fusion proteins were also tested for their specific binding and non-binding to a panel of monoclonal antibodies, as shown in FIGS. 10 & 11. FIGS. 10A-10F are graphical representations of antibody reactivity to the Kennedy loop-GFP recombinant fusion proteins: K-CTcc, K-NTcc, K-SARcc, K-SARcc, MPER-C, and gp41MN, respectively, using a panel of known anti-HIV-1 envelope monoclonal antibodies, according to an exemplary embodiment. These graphs demonstrate the binding of the Kennedy Loop-GFP recombinant fusion protein as determined by specific reactivity to a panel of known anti-HIV-1 envelope monoclonal antibodies. Only those monoclonal antibodies which showed reactivity had their specific epitope present in a given recombinant fusion protein. All the tests were done in triplicates using ELISA. FIGS. 11A-11C are graphical representations of antibody reactivity to the scrambled Kennedy loop-GFP recombinant fusion proteins: Scram-K-CTcc, Scram-K-NTcc, Scram-K-SARcc, respectively, using a panel of known anti-HIV-1 envelope monoclonal antibodies. These graphs show the lack of binding of the scrambled Kennedy Loop-GFP recombinant fusion protein to a panel of known anti-HIV-1 monoclonal antibodies. None of the monoclonal antibodies tested showed any reactivity to the scrambled recombinant fusion protein except for the anti-His Ab, because all the recombinant fusion proteins generated were tagged with His-Tag for purification purposes. All tests were done in triplicates using ELISA.

Isolation of the Epitope-Specific B Cells

Figure 12:
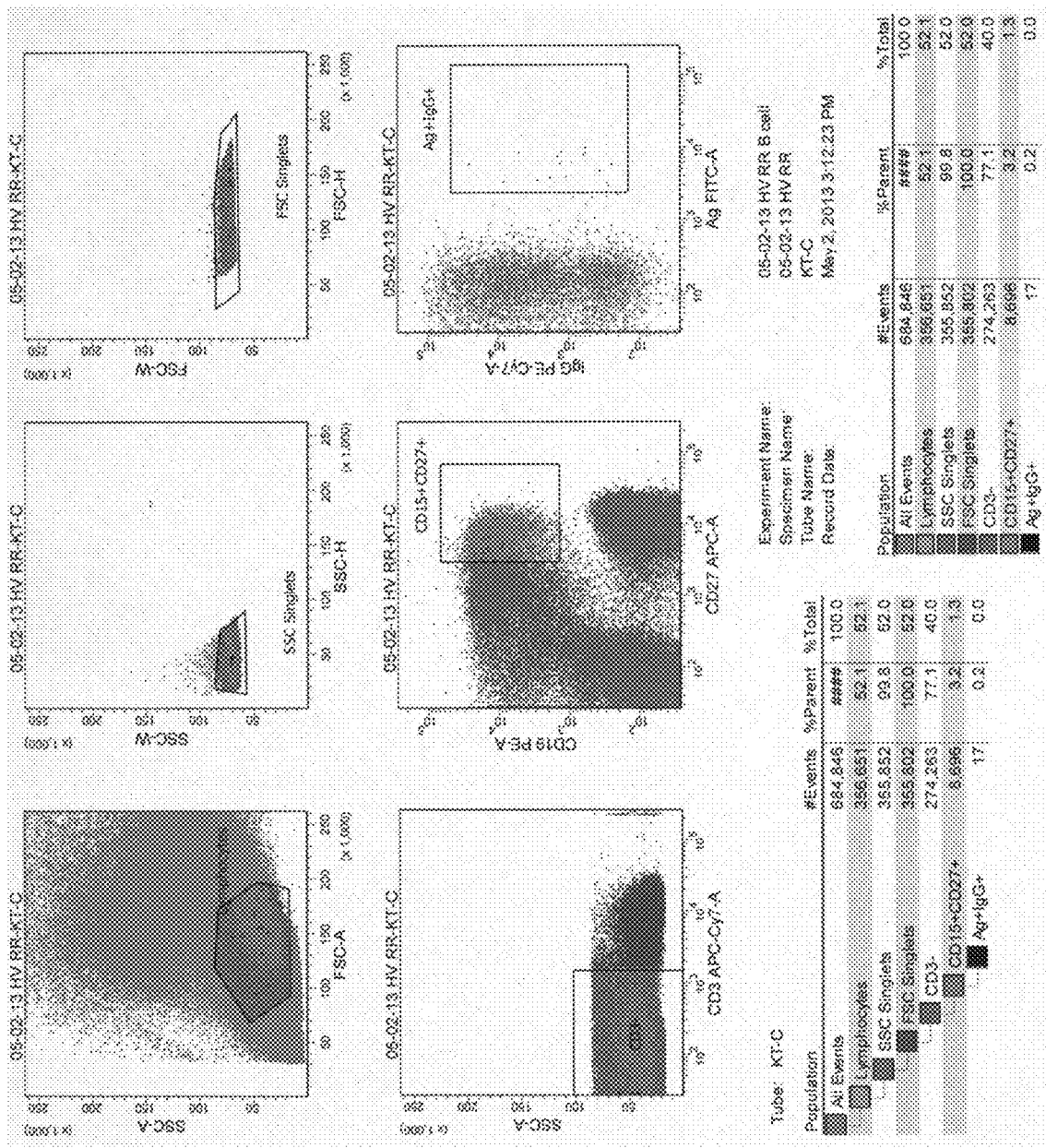
FIG. 12 is a set of images from the FACS sorting of B cells specific for the Kennedy Loop-GFP recombinant fusion proteins, according to an exemplary embodiment.
Figure 13:
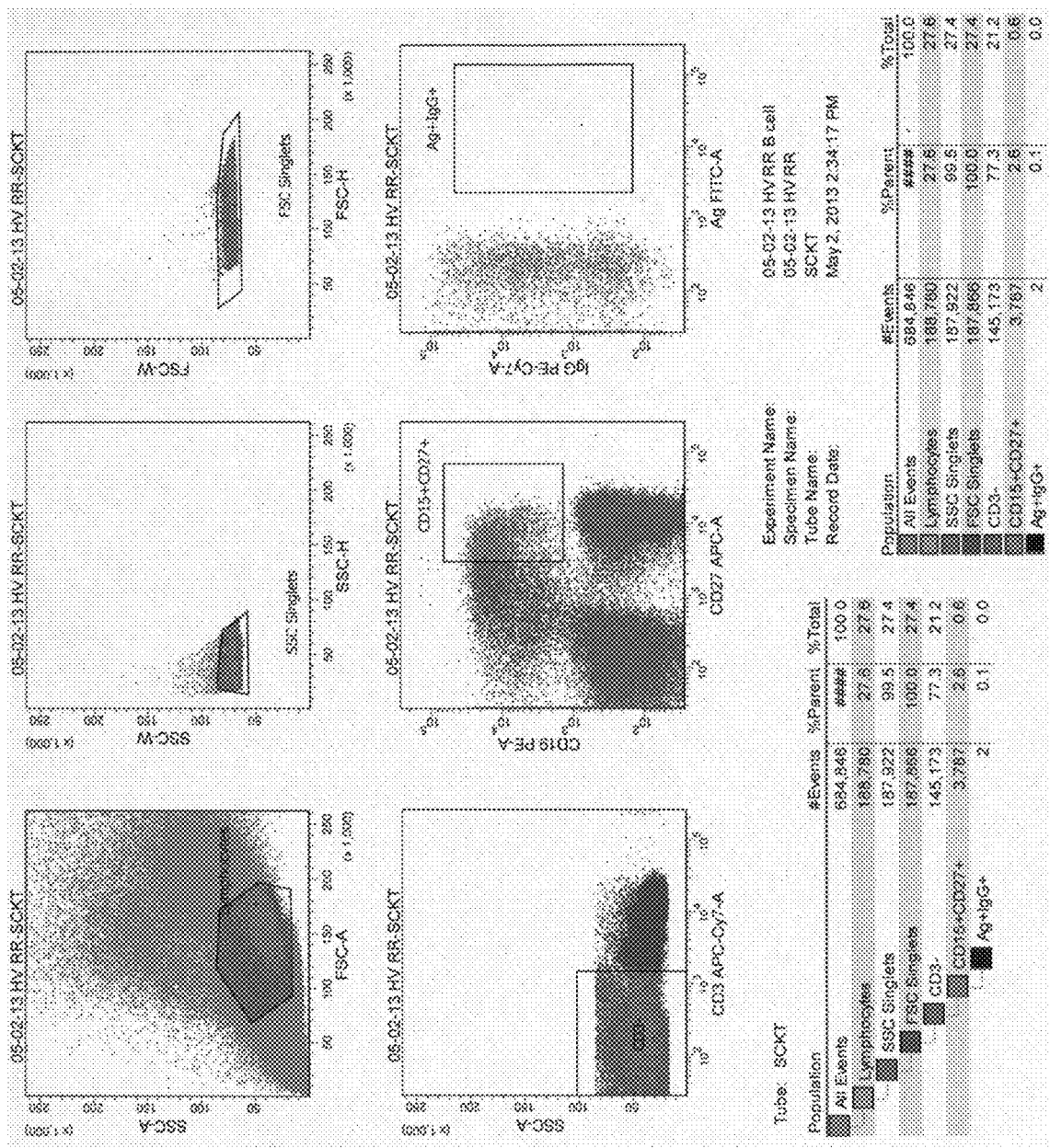
FIG. 13 is a set of images from the FACS sorting of B cells using the scrambled Kennedy Loop-GFP recombinant fusion proteins, according to an exemplary embodiment.

Four years after the vaccination, the vaccine-protected rhesus monkeys were boosted with the two out of the three original immunogens (trimeric clade C HIV1084i gp160 and HIV-1 Tat) to expand the memory B cell pool. The antigens (trimeric HIV-1 1084i gp160 and HIV-1 Tat) were the exact same immunogens (even same batch) that those used for vaccination. Additionally, Gag-Pol particles had been part of the vaccine regimen but were not included in the boost. FACS sorting for single memory B cells was done 14 days after the vaccine boost in rhesus monkey #RTr-11. K-CTcc fused to GFP was used as a recombinant bait protein for the isolation of cognate memory B cells from PBMC of rhesus monkey #RTr-11. Live cell flow cytometry sorting for single memory B cells was performed 14 days after the vaccine boost in rhesus monkey #RTr-11. Kennedy Loop-specific single memory B cells were sorted into a PCR plate as follows: CD3⁻, CD19⁺, CD27⁺, IgG⁺ and K-CTcc-GFP⁺ cells (FIG. 12). Out of 0.68 million PBMC, 17 memory B cells were found to be highly specific to the K-CTcc protein. For the sorting experiment, 5×10⁷ PBMC were used and the cytometer was programmed to collect 90 individual CD3⁻, CD19⁺, CD27⁺, IgG⁺ and K-CTcc-GFP⁺ cells at one cell per well in the plate. Epitope-specific cells represented approximately 1.3% of the memory B cells. As many as 90 K-CTcc-specific IgG-positive memory B cells were sorted in plate 1 (p1). Control staining with scrambled-K-CTcc was carried out to set the baseline for sorting. Only one non-specific cell was detected in 0.68 million cells analyzed, which was possibly due to autofluorescence (as shown in FIG. 13).

The B cells sorted with fluorescently-tagged K-CTcc were used to generate recombinant monoclonal antibodies. Using single-cell cDNA synthesis and nested PCR for IgG-specific gene amplification, we were able to isolate 29 gamma, 12 kappa and 17 lambda genes. After cDNA synthesis, light chain variable (VL) Ig genes and heavy chain variable (VH) Ig genes were amplified by semi-nested PCR with a set of newly developed primers specific to rhesus monkey VL and VH Ig genes. Primers for amplification of rhesus monkey immunoglobulin VH and VL genes were selected as previously described in Sholukh A M, et al. (2012) (Isolation of Monoclonal Antibodies with Predetermined Conformational Epitope Specificity. PLoSONE 7(6): e38943. doi:10.1371/journal.pone.0038943).

TABLE 1

Primers used for antibody gene amplification.

| Forward primer | 5'-3' sequence |
| --- | --- |
| VH-1 | SAGGWSCAGCTGGTRCAATCCGG |
| VH-2 | CAGGTGACCTTGAAGGAGTCTGG |
| VH3/5/7 | SAGGTGCAGYTGGTGSAGTCTGG |
| VH4/6 | CAGGTGCARCTGCAGGAGTCRGG |
| VH-5 | GAGGTGCAGCTGGTGCAGTCTGG |
| VH-6 | CAGGTACAGCTGCAGCAGTCAGG |
| VH-7 | CAGGTGCAGCTGGTGCAATGTGG |
| Vλ-1 | CAGTCTGTRCTGACVCAGCCDCC |
| Vλ-2 | CAGKCTGCCCYGAYTCAGYCTCC |
| Vλ-3A | TCCTCTGGGCTGACTCAG |
| Vλ-3B | TCCTMTGAGCTGACACAGCCDCC |
| Vλ-4 | CAGCYTGTGCTGACTCARTCGCC |
| Vλ-5 | MAGSCTRTGCTGACTCAGCCRRC |
| Vλ-6 | AATTTTATGCTGACTCAGCCC |
| Vλ-8/7 | CAGACTGTGGTGACYCAGGAGYC |
| Vλ-9 | CAGCYTGTGCTGACTCARCCACC |
| Vλ-10 | CAGGCAGGGCTGACTCAGCCACC |
| Vκ-1 | GACATYCAGATGWCCCAGTCTCC |
| Vκ-2 | GATAYTGTGATGACCCAGACTCC |
| Vκ-3 | SAAATWGTRWTGACKCAGTCTCC |
| Vκ-4 | GACATYGTGMTGACCCAGTCTCC |
| Vκ-5 | GAAACGACACTCACGCAGTCTCC |
| Vκ-6 | GAWRTTGTGMTGACWCAGTCTCC |
| Vκ-7 | GACATTGTGCTGACCCAGTCTCC |
| Reverse primer | 5'-3' sequence |
| γ-PCR1 | GGACAGCCKGGAAGGTGTGC |
| γ-PCR2 | GCCTGAGTTCCACGACACGGTCAC |

TABLE 1 -continued

Primers used for antibody gene amplification.

| | |
|---|---|
| λ-PCR1 | CCGCGTACTTGTTGTTGCTCTGT |
| λ-PCR2 | CAGAGGAGGGCGGGAASAGA |
| κ-PCR1 | GAGGCAGTTCCAGATTTCAA |
| κ-PCR2 | GGTGCAGCCACAGCTCGTTTGAT |

N=A+G+C+T; V=A+C+G; D=A+T+G; B=T+C+G; H=A+T+C; W=A+T; S=C+G; K=T+G; M=A+C; Y=C+T; R=A+G.

Using these primers under the experimental conditions above, about 29 gamma, 12 kappa and 17 lambda genes were isolated. The pairs of VH and VL genes obtained after two rounds of PCR were sequenced to assess productivity and gene rearrangement as well as to obtain sequence information for the beginning of framework region 1 (FR1). After amplification of VH/VL pairs with cloning primers, the PCR fragments were inserted into vectors of the pFUSE2-family that contain constant region sequences of human Ig light (Igk or Ig12) or heavy (Igc1) chains. This cloning strategy yielded chimeric simian-human IgG1 monoclonal antibodies.

About 10 pairs of full-length Ab genes were cloned into commercial vectors in the first round of screening. Antibody genes from those single B cells that were able to provide a pair of VH and VL genes (gamma with kappa or gamma with lambda) by nested PCR were cloned into pFUSE2 vectors (as shown in FIG. 14). In case of monoclonality, one VH gene will be amplified along with either a kappa or a lambda VL but not both. FIG. 14 shows the yield of anti-Kennedy Loop monoclonal antibodies generated from single B cells sorting and amplification of antibody variable genes. Sequences of the full-length monoclonal antibodies are as follows:

FIG. 15 is the sequence listing of the variable heavy (VH) chain gene sequence and the constant heavy (CH) chain gene sequences of mAb 61p1B2.

FIG. 16 is the sequence listing of the variable light (VL) chain gene sequence and the constant light (CL) chain gene sequences of mAb 61p1B2.

FIG. 17 is the sequence listing of the variable heavy (VH) chain gene sequence and the constant heavy (CH) chain gene sequences of mAb 61p1C5.

FIG. 18 is the sequence listing of the variable light (VL) chain gene sequence and the constant light (CL) chain gene sequences of mAb 61p1C5.

FIG. 19 is the sequence listing of the variable heavy (VH) chain gene sequence and the constant heavy (CH) chain gene sequences of mAb 61p1E2.

FIG. 20 is the sequence listing of the variable light (VL) chain gene sequence and the constant light (CL) chain gene sequences of mAb 61p1E2.

FIG. 21 is the sequence listing of the variable heavy (VH) chain gene sequence and the constant heavy (CH) chain gene sequences of mAb 61p1F4.

FIG. 22 is the sequence listing of the variable light (VL) chain gene sequence and the constant light (CL) chain gene sequences of mAb 61p1F4.

FIG. 23 is the sequence listing of the variable heavy (VH) chain gene sequence and the constant heavy (CH) chain gene sequences of mAb 61p1D3.

FIG. 24 is the sequence listing of the variable light (VL) chain gene sequence and the constant light (CL) chain gene sequences of mAb 61p1D3.

Embodiments of the disclosure include isolated HIV monoclonal antibodies, or antigen binding fragment thereof, containing a heavy chain and a light chain. In certain embodiments, the heavy chain includes a heavy chain variable region with an amino acid sequence at least 80% identical to one of the amino acid sequences set forth in FIGS. 15, 17, 19, 21, and 23. In certain embodiments, the heavy chain includes a heavy chain variable region with an amino acid sequence at least 90% identical to one of the amino acid sequences set forth in FIGS. 15, 17, 19, 21, and 23. In certain embodiments, the heavy chain includes a heavy chain variable region with an amino acid sequence at least 95% identical to one of the amino acid sequences set forth in FIGS. 15, 17, 19, 21, and 23. In certain embodiments, the light chain includes a light chain variable region with an amino acid sequence at least 80% identical to one of the amino acid sequences set forth in FIGS. 16, 18, 20, 22, and 24. In certain embodiments, the light chain includes a light chain variable region with an amino acid sequence at least 90% identical to one of the amino acid sequences set forth in FIGS. 16, 18, 20, 22, and 24. In certain embodiments, the light chain includes a light chain variable region with an amino acid sequence at least 95% identical to one of the amino acid sequences set forth in FIGS. 16, 18, 20, 22, and 24.

Small Scale Expression

Small scale expression after co-transfection of 293T cells revealed expression of 4 monoclonal antibodies. Full-length IgG1 monoclonal antibodies were produced by transient co-transfection of the paired heavy and light chain pFUSE plasmids into Expi293F cells (Invitrogen) grown in serum-free FreeStyle™ 293Expression Medium (GibcoH Invitrogen) using the TransITPRO™ Transfection Kit (Mirus Bio). Cells were cultivated for 4 days at 37° C./8% CO2 with continuous shaking at 135 rpm. Supernatants were collected, filtered through 0.22 µm filters and supplemented with Halt Protease Inhibitor Cocktail (ThermoFisher) and 1006 penicillin-streptomycin solution (GibcoH Invitrogen). Next, supernatants were tested for binding to HIV-1 env and mimotopes, and positive monoclonal antibodies were affinity-purified using protein A agarose (GE Healthcare) according to manufacturer's instructions. IgG concentrations were determined by measuring absorbance at 280 nm on Nanodrop 1000 (Thermo Scientific) using the IgG default protocol. In previous attempts using linear mimotopes without C-C constraints, most of the monoclonal antibodies generated from single-cell sorted memory B cells did not show the expected specificity for the bait protein(s) and/or HIV-1 env or peptides thereof.

Large Scale Expression

Glycerol stocks of bacterial cultures with mAb plasmids were expanded to make midi and maxi preps; plasmids were used to transfect large cultures of Expi293F cells to produce glycosylated full-length monoclonal antibodies. These were expressed (yield 5 to 10 µg/ml) and purified using protein A affinity chromatography.

Figure 25:
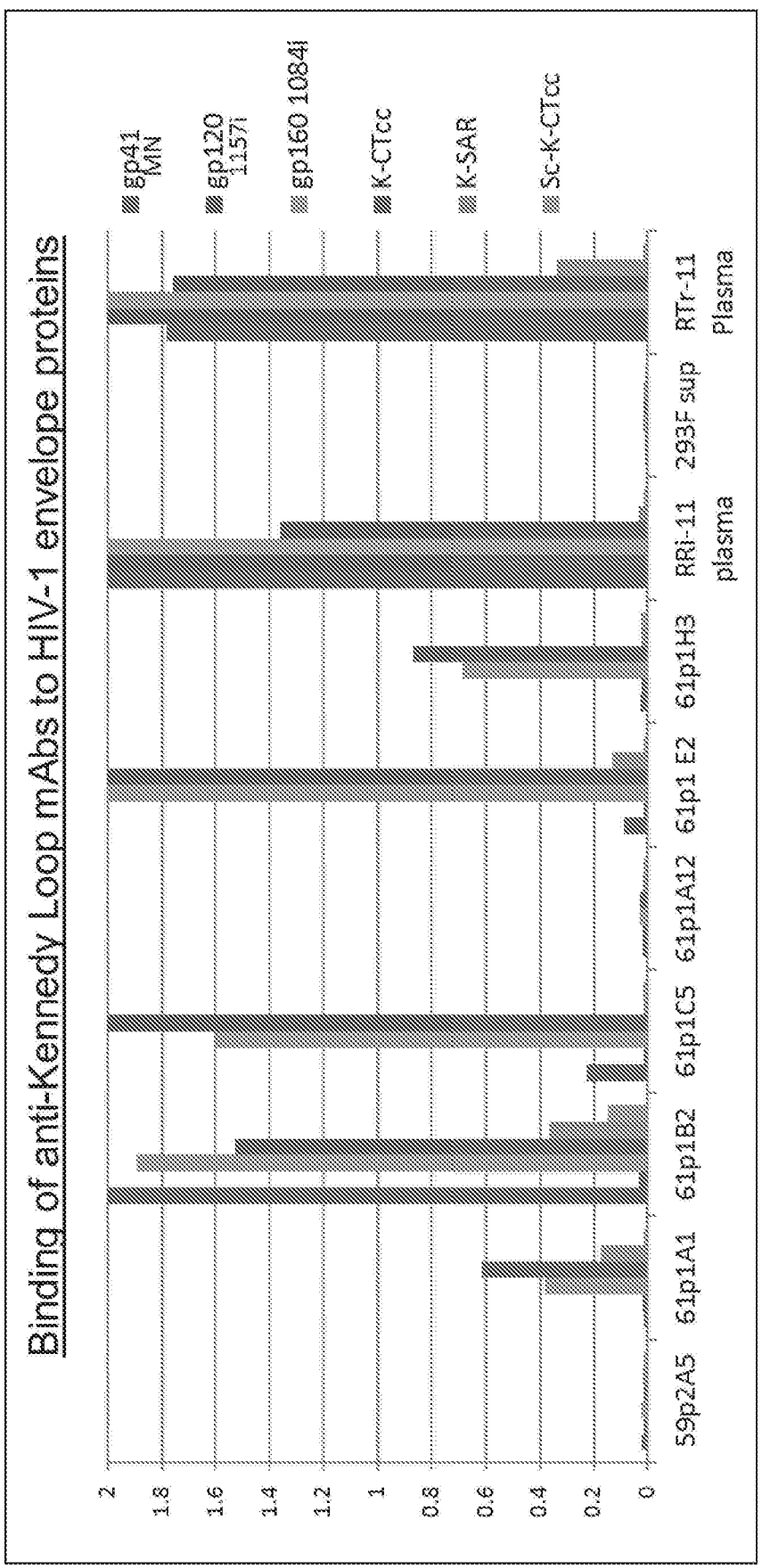
FIG. 25 is a graphical representation of the binding assays of the anti-Kennedy loop monoclonal antibodies to HIV-1 envelope proteins, according to an exemplary embodiment.

At least seven monoclonal antibodies were tested and were analyzed for specific binding to Kennedy Loop-GFP mimotopes, native Kennedy Loop-GPF fusion protein, and gp41 or gp160 of some HIV envelopes. Monoclonal antibodies, which showed specific binding to consensus HIV-1 clade C env peptides representing the Kennedy Loop region, were identified. Six anti-Kennedy Loop monoclonal antibodies were tested for their binding efficacy. Binding of anti-Kennedy Loop monoclonal antibodies to HIV-1 envelope proteins obtained from the NIH AIDS Research and Reference Reagent Program (ARRRP) was analyzed. Five of them showed specific binding to K-CTcc and HIV-1 gp160, as shown in FIG. 25. Plasma samples from animals RRi-11 and RTr-11 were used as positive controls. The monoclonal antibodies were also subjected to epitope determination, as shown in FIG. 26, using specific binding to consensus HIV-1 clade C env peptides representing the Kennedy Loop region as read-out. FIG. 26 is a schematic representation of the epitope mapping of the anti-Kennedy loop monoclonal antibodies.

In Vitro Neutralization

Neutralization by TZM-bl cell-based assays was not observed, but the monoclonal antibodies did show virus neutralization in human peripheral blood mononuclear cell (PBMC)-based assays. TZM-bl cell based assay utilize a genetically engineered cell line (TZM-bl) that are susceptible to infection by most strains of HIV-1, SIV, and SHIV. This assay as many other assays is based on the same principle, measuring reductions in virus infectivity as described in Curr. Protoc. Immunol. 2005 January; Chapter 12: Unit 12.11. doi: 10.1002/0471142735.im1211s64 by D. Montefiori. However, TZM-bl cells display an abnormally high number of CCR5 coreceptor molecules on the cell surface, which yield false positive neutralization data for a number of anti-gp41 neutralizing monoclonal antibodies, especially those with a relatively slow on-rate.

The newly isolated anti-Kennedy Loop monoclonal antibodies had no reactivity to self-antigens, such as ds DNA, SM proteins, RNPs, SS-B/La antigens, cardiolipin, and SS-A/Ro antigens and were negative against scrambled sequences of Kennedy Loop proteins. Auto reactivity was tested with an anti-dsDNA EIA kit, anti-Sm/RNP EIA kit, anti-Sm EIA kit, autoimmune EIA anti-SS-A/Ro Test, autoimmune EIA anti-SS-B/La test, Bio-Rad Kallestad ANA screen (all Bio-Rad) and QUANTA LiteH ACA IgG III (INOVA Diagnostics). Assays were performed on automated PhD System (Bio-Rad) and DSXTM System (Dynex Technologies).

Monoclonal antibodies did not bind to or capture virion as expected. ELISA plates (Nunc) were coated with 5 μg/ml of goat anti-human IgG Fc specific Ab (Jackson Immuno Research) overnight at 4° C. After blocking and washing, monoclonal antibodies were added at 5 μg/ml and incubated for 2 hours. The plates were washed, SHIV-1157ipELp (the SHIV strain that had been used as challenge virus in the vaccinated rhesus monkeys earlier) was added to the monoclonal antibodies and incubated for 20 hours, after which the plates were washed again and incubated with 0.5% Triton X-100 for 1 hour to release p27 from the virus bound to the various monoclonal antibodies. The amount of p27 released was determined using a p27 SIV capture kit (ABL, Inc).

Figure 27:
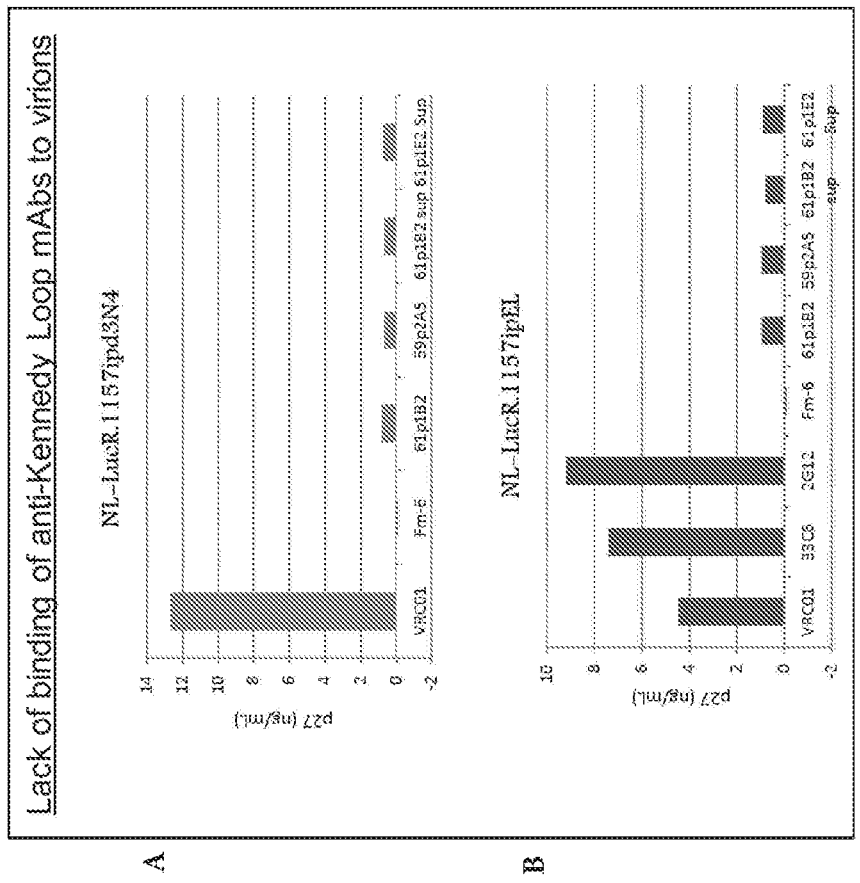
FIGS. 27A and 27B are graphical representations of the virion capture assays on two different viruses, according to an exemplary embodiment.

The non-binding of anti-Kennedy Loop monoclonal antibodies to virions was expected, because the Kennedy Loop is not exposed on intact virions. Rather, the Kennedy Loop is transiently exposed at the time of either virus entry into or exit from host cells. During this transient phase, structural changes in the HIV-1 env trimer lead to unfolding of some env domains. The Kennedy Loop is thought to appear transiently on the cell surface thereby giving antibodies a chance to hit otherwise unexposed target epitopes crucial for viral entry into the cells. Virion capture experiments were performed multiple times, even with improved, bead-based techniques and including multiple controls. FIGS. 27A and 27B are graphical representations of the virion capture assays on two different viruses: NL-LucR.1157ipd3N4 and NL-Luc.R.1157ipEL. Specific monoclonal antibodies were used in these assays. MAb VRCO1 (anti-CD4 binding site), mAb 33C6 (anti-V3 loop of HIV-1 gp120) and 2G12 (anti-glycan on HIV-1 gp120) were used as positive controls. MAb Fm-6 (anti-SARS) was used as a negative isotype control. The anti-Kennedy Loop monoclonal antibodies showed approximately 5% binding to cells inoculated with virus. This is consistent with the transient appearance of the Kennedy Loop on the cell surface. Otherwise, the Kennedy Loop is located intracellularly as part of the cytoplasmic tail of gp41.

Figure 28:
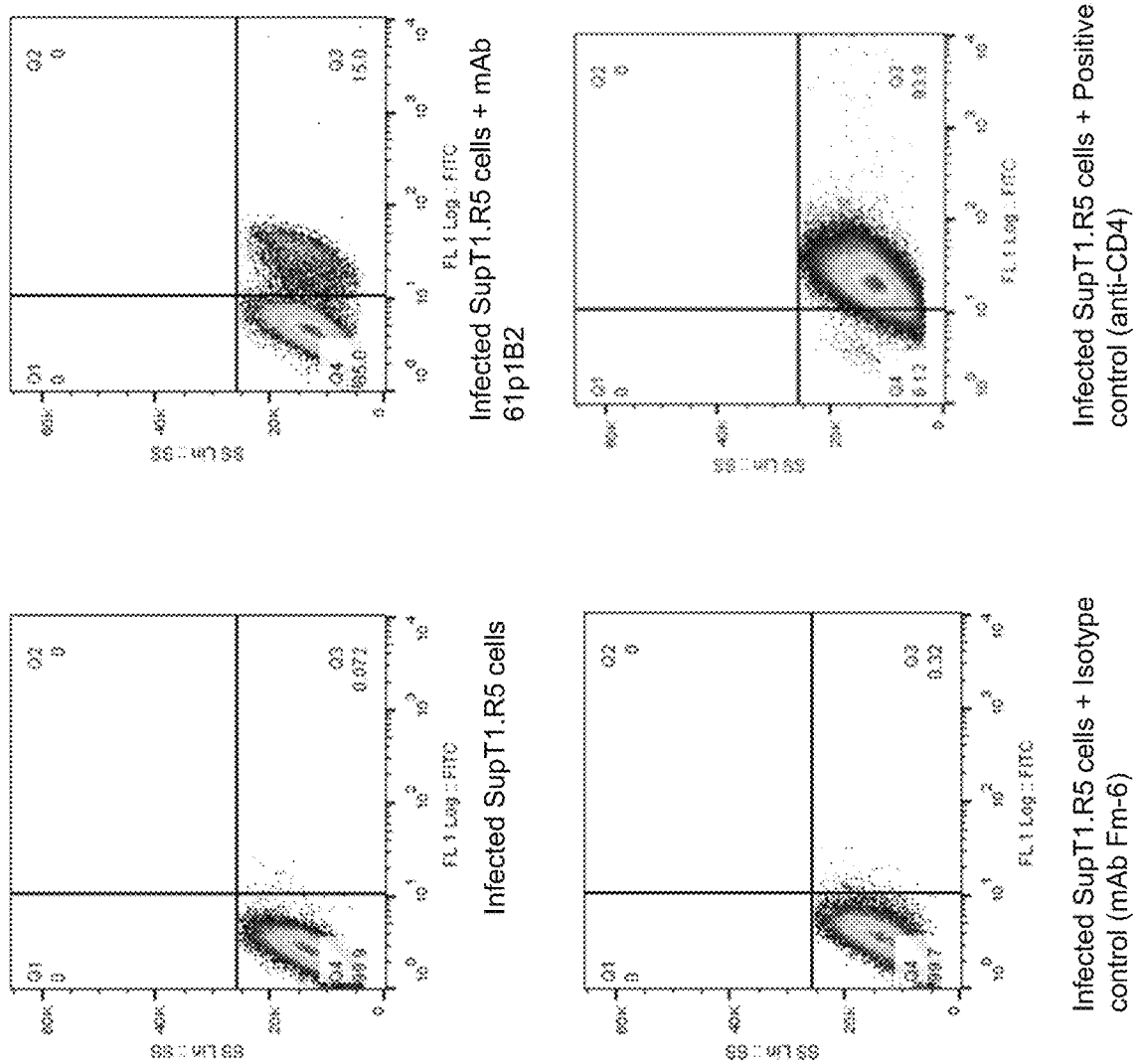
FIG. 28 is a set of images from the flow cytometry analysis of the cell surface binding of mAb 61p1B2 to infected cells, according to an exemplary embodiment.

Engineered SupT1 cells overexpressing CCR5 receptors (SupT1.R5) were exposed to a high inoculum of HIV-1 (in this case HIV-1 1084i) and incubated for 48 h. Cells were then incubated with anti-Kennedy Loop monoclonal antibodies or isotype controls for 1 hour at 4° C. followed by binding to goat anti-human Fc FITC-labeled antibody. Cells were fixed and kept for flow cytometry. Simultaneously, a control experiment was also run on non-infected cells to rule out any background issues. Results of one of the representative assay are shown in FIG. 28 that demonstrates the cell surface binding of mAb 61p1B2 to infected cells as assessed by flow cytometry.

Figures 29A, 29B:
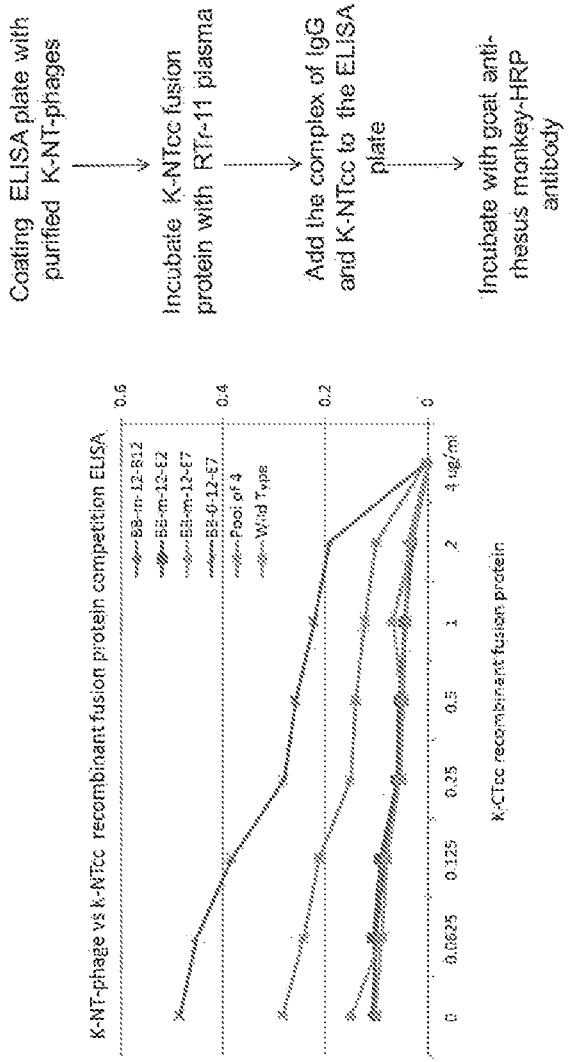
FIG. 29A is graphical representation of a competition ELISA assay, according to an exemplary embodiment
FIG. 29B is flowchart of the methodology used for the assay.
Figure 30:
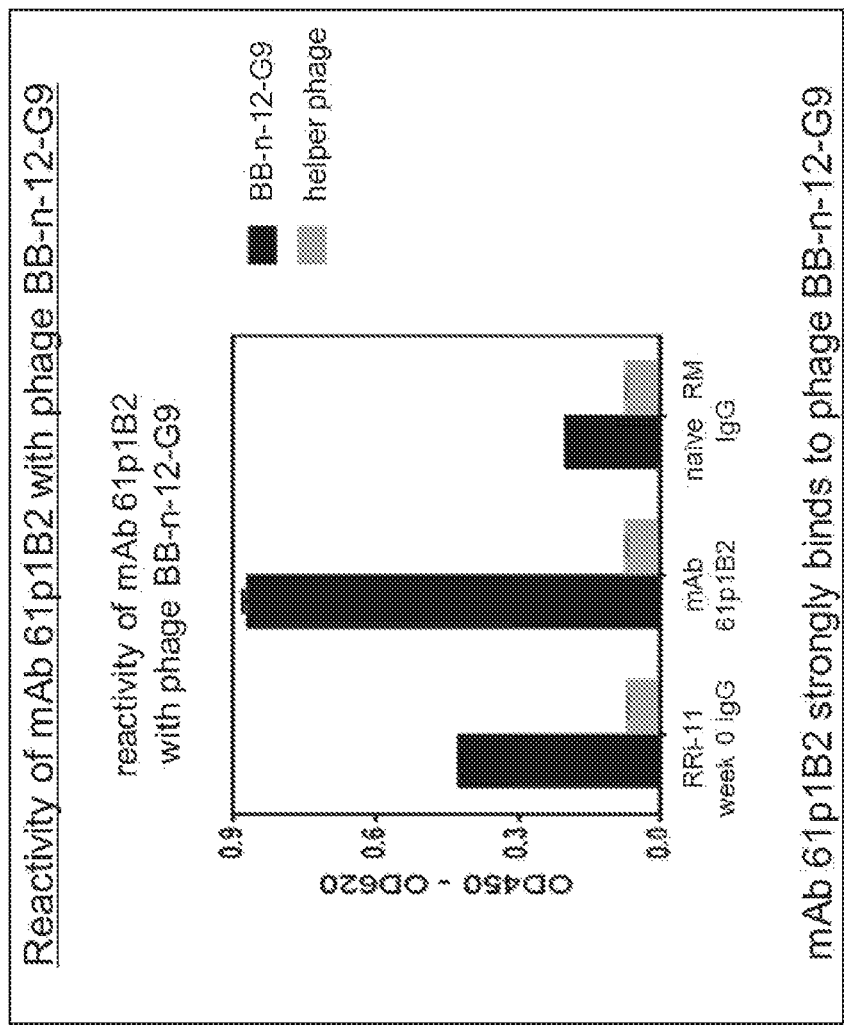
FIG. 30 is a graphical representation of the specific binding of the anti-Kennedy Loop mAb 61p1B2 to a mimotope-phage corresponding to Kennedy-C terminal region (K-CTcc).

Monoclonal antibodies exhibiting competitive inhibition between Kennedy Loop-GFP recombinant fusion protein and recombinant bacteriophage displaying the Kennedy epitope were isolated from a vaccine-protected rhesus monkey. Competition phage ELISA was performed between K-NTcc recombinant fusion protein and the recombinant phages bacteriophages displaying Kennedy-region mimotopes that had been isolated from vaccine-protected rhesus monkeys. The names of the mimotopes are listed in the right upper corner of the graph in FIG. 29A. The methodology for the competitive inhibition experiment was described as a flow chart in FIG. 29B. Results of a competitive inhibition assay performed using K-NTcc competing with purified mimotope phages representing the Kennedy Loop sequence are presented in FIG. 29A. This experiment showed a strong direct correlation between Kennedy Loop-GFP recombinant fusion protein and the protection-linked mimotopes obtained from vaccine-protected rhesus monkeys. FIG. 30 is a graphical representation of the binding of the anti-Kennedy Loop mAb 61p1B2 to a mimotope-phage corresponding to K-CTcc region. RRi-11 plasma was used a positive control and naïve rhesus monkey plasma as a negative control in this assay.

Figure 31:
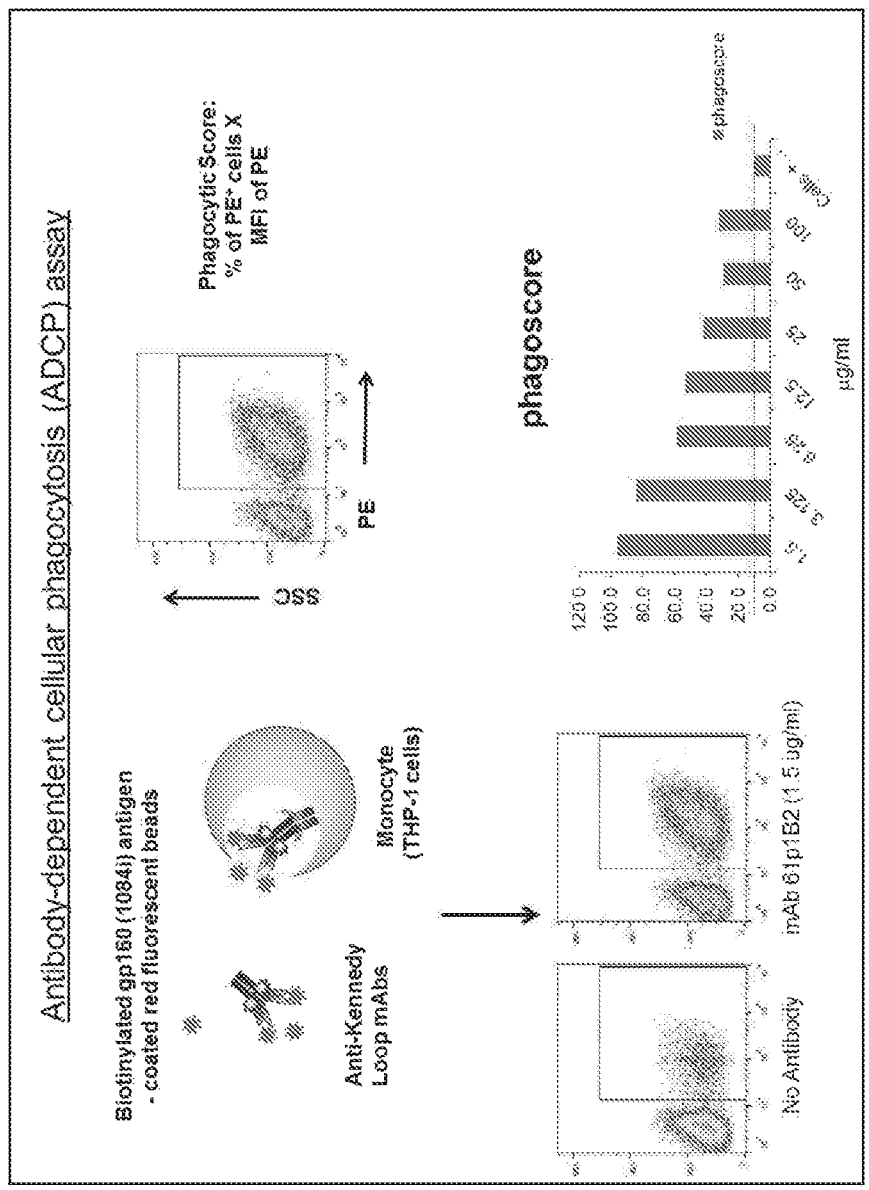
FIG. 31 is a schematic representation of antibody-dependent cellular phagocytosis (ADCP) assays using mAb 61p1B2 and the results obtained, according to an exemplary embodiment.
Figure 32:
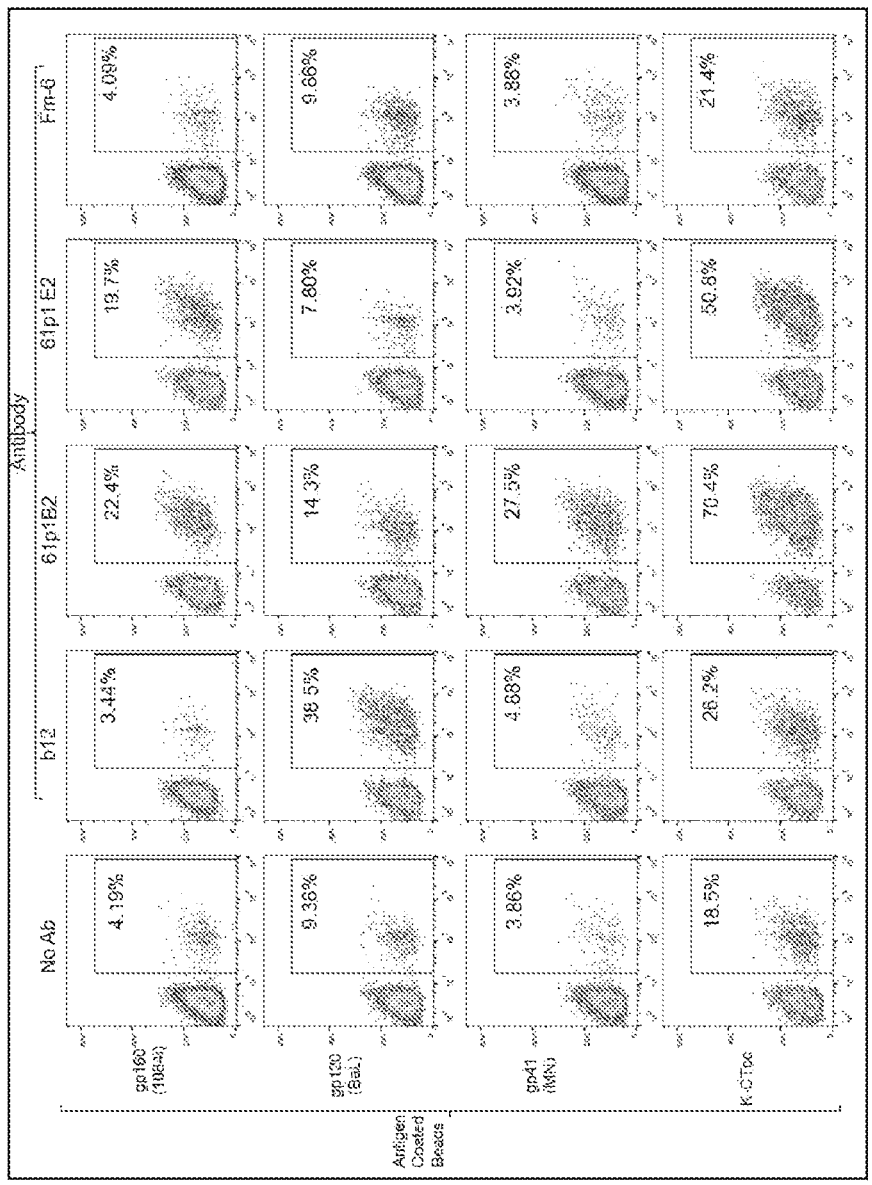
FIG. 32 is a set of analysis from the antibody-dependent cellular phagocytosis assay using mAb 61p1B2, mAb 61p1E2, and control monoclonal antibodies (mAb b12 and mAB Fm-6) as ADCP positive and negative assay controls, respectively.

Strong antibody-dependent phagocytosis (ADCP) was observed in the presence of these monoclonal antibodies. Monoclonal antibodies were incubated with inert fluorescent beads coated with gp160 antigen. After 1 hour, the samples were incubated with THP-1 monocytic cells, and about 12 to 24 hours later, the cells were fixed and analyzed on flow cytometry. FIG. 31 is a schematic representation of antibody-dependent cellular phagocytosis (ADCP) assays using mAb 61p1B2 and the results obtained. FIG. 32 is a set of analysis from the ADCP assay using MAb 61p1B2, MAb 61p1E2, and control monoclonal antibodies (mAb b12 and mAB Fm-6) as ADCP positive and negative assay controls, respectively. MAb 61p1B2 showed strong phagocytosis in the presence of beads coated with K-CTcc, HIV-1 gp41 MN and gp160 1084i. MAb 61p1E2 showed strong phagocytosis only in presence of K-CTcc. Monoclonal antibodies, mAb b12 and mAB Fm-6, were used as ADCP positive and negative assay controls, respectively.

The link of antibodies to the gp41 Kennedy Loop with vaccine-induced protection demonstrates the suitability of this region for vaccine design. Embodiments described here include isolation and characterization of the selective monoclonal antibodies with the use of several Kennedy Loop-based mimotopes. Those skilled in the art will recognize, or be able to ascertain using no more than routine experimentation, many equivalents to the specific embodiments of the disclosure described herein. Such equivalents are intended to be encompassed by the following claims.

What is claimed is:

1. A vaccine composition effective against a Human Immunodeficiency Virus-1 (HIV-1) infection, the composition comprising:
   a recombinant peptide sequence having at least 90% or more sequence identity to C-terminal domain of Kennedy loop of a HIV-1 gp41 protein and being conformationally constrained by a two or more terminal cysteine residues,
   wherein the C-terminal domain is positions 43 to 66 of any one of:

(SEQ ID NO: 31)
   WYIKIFIMIVGGLIGLRIXFAVLSIVNRVRQGYSPLSFQTHLPAPRGPDRPEGIEEEGGERDRDRSI;

(SEQ ID NO: 32)
   WYIKIFIMIIGGLIGLRIVFSVLSIMNRVRQGYSPLSFQTHLPASRGPDRPGGIEEEGGERDRDRSG;

(SEQ ID NO: 33)
   WYIKLFEVIIVGGLVGLRIVFAVLSIVNRVRQGYSPLSFQTHLPIPRGPDRPEGIEEEGGERGRDRSI;

(SEQ ID NO: 34)
   WYIKLFEVIIVGGLVGLRIVFAVLSIVNRVRQGYSPLSFQTHLPIPRGPDRPEGIEEEGGERGRDRSI;

(SEQ ID NO: 35)
   WYIKIFIMIVGGLIGLRIIFAVLSIVNRVRQGYSPLSFQTHLPLPRGADRPEGIEEEGGERDRDRSI;

(SEQ ID NO: 36)
   WYIKIFIMIVGGLIGLRIIFAVLSIVSRVRQGYSPLSFQTHLPTPRGPDRPEGIEEEGGERDRDRSI;

(SEQ ID NO: 37)
   WYIRIFIMIVGGLIGLRIIFAVLSIVNRVRQGYSPLSFQTLTPNPRELDRLRGIEEEGGEQDKDRSI;

(SEQ ID NO: 38)
   WYIKIFIMIVGGLVGLRIVFTVLSIVNRVRQGYSPLSFQTRFPAPRGLDRPEGIEEEGGERDRDRSR;
   and (SEQ ID NO: 39)
   WYIKIFIMIVGGLIGLRIIFAVLSMVNRVRQGYSPLSFQTLTPNPRGPDRLGRIEEEGGEQDRDRSI.

2. A vaccine composition effective against a Human Immunodeficiency Virus-1 (HIV-1) infection, the composition comprising:
   a recombinant peptide sequence with at least 90% or more sequence identity to N-terminal domain of the Kennedy loop of the HIV-1 gp41 protein and being conformationally constrained by a two or more terminal cysteine restudies,
   wherein the N-terminal domain is positions 27 to 44 of any one of:

(SEQ ID NO: 31)
   WYIKIFIMIVGGLIGLRIXFAVLSIVNRVRQGYSPLSFQTHLPAPRGPDRPEGIEEEGGERDRDRSI;

(SEQ ID NO: 32)
   WYIKIFIMIIGGLIGLRIVFSVLSIMNRVRQGYSPLSFQTHLPASRGPDRPGGIEEEGGERDRDRSG;

(SEQ ID NO: 33)
   WYIKLFEVIIVGGLVGLRIVFAVLSIVNRVRQGYSPLSFQTHLPIPRGPDRPEGIEEEGGERGRDRSI;

(SEQ ID NO: 34)
   WYIKLFEVIIVGGLVGLRIVFAVLSIVNRVRQGYSPLSFQTHLPIPRGPDRPEGIEEEGGERGRDRSI;

(SEQ ID NO: 35)
   WYIKIFIMIVGGLIGLRIIFAVLSIVNRVRQGYSPLSFQTHLPLPRGADRPEGIEEEGGERDRDRSI;

(SEQ ID NO: 36)
   WYIKIFIMIVGGLIGLRIIFAVLSIVSRVRQGYSPLSFQTHLPTPRGPDRPEGIEEEGGERDRDRSI;

(SEQ ID NO: 37)
   WYIRIFIMIVGGLIGLRIIFAVLSIVNRVRQGYSPLSFQTLTPNPRELDRLRGIEEEGGEQDKDRSI;

(SEQ ID NO: 38)
   WYIKIFIMIVGGLVGLRIVFTVLSIVNRVRQGYSPLSFQTRFPAPRGLDRPEGIEEEGGERDRDRSR;
   and (SEQ ID NO: 39)
   WYIKIFIMIVGGLIGLRIIFAVLSMVNRVRQGYSPLSFQTLTPNPRGPDRLGRIEEEGGEQDRDRSI.

* * * * *